US007011947B2

(12) United States Patent
Golub et al.

(10) Patent No.: US 7,011,947 B2
(45) Date of Patent: Mar. 14, 2006

(54) MLL TRANSLOCATIONS SPECIFY A DISTINCT GENE EXPRESSION PROFILE, DISTINGUISHING A UNIQUE LEUKEMIA

(75) Inventors: Todd R. Golub, Newton, MA (US); Scott A. Armstrong, Wayland, MA (US); Stanley J. Korsmeyer, Weston, MA (US)

(73) Assignees: Whitehead Institute for Biomedical Research, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 332 days.

(21) Appl. No.: 10/198,064

(22) Filed: Jul. 17, 2002

(65) Prior Publication Data

US 2003/0134300 A1 Jul. 17, 2003

Related U.S. Application Data

(60) Provisional application No. 60/306,103, filed on Jul. 17, 2001.

(51) Int. Cl.
C12Q 1/68 (2006.01)
C12Q 1/02 (2006.01)
G01N 33/53 (2006.01)

(52) U.S. Cl. ............................... 435/6; 435/7.1; 435/29

(58) Field of Classification Search .................. 435/6, 435/7.1, 29

See application file for complete search history.

(56) References Cited

U.S. PATENT DOCUMENTS

| 5,605,805 A | 2/1997 | Verwer et al. |
| 5,998,136 A | 12/1999 | Kamb |
| 6,190,857 B1 | 2/2001 | Ralph et al. |

OTHER PUBLICATIONS

Lahm, H. et al. "Comprehensive galectin fingerprinting in a panel of 61 human tumor cell lines by RT–PCR and its implications for diagnostic and therapeutic procedures", May 1991, J. Cancer Res. Clin. Oncol., vol. 127: p. 375–386.*
Chang, YY et al., "The effect of galectin–1 on 3T3 cell proliferation on chitosan membranes", 2004, Biomaterials, vol. 25: p. 3603–3611.*
Armstrong, S.A., et al., "The MLL Dependent Gene Expression Profile: Characterization of a Unique Leukemia and Identification of a Potential Molecular Therapeutic Target," Blood, 98 (11 Part 1):800a (2000).
Chi, Hyun–Sook, et al., "Internal Tandem Duplication of the FLT3 Gene in Acute Leukemia: Clinical and Prognostic Implications in Acute Myeloid Leukemia," Blood, 96 (11 Part 1):104a (2000).

Imamura, T., et al., "Detection of MLL–AF5q31 Fusion Transcript in an Infantile Acute Lymphoblastic Leukemia Cell Line," Blood, 98 (11 Part 2):168b (2001).
Kawagoe, H., et al., "Targeted Down–Regulation of MLL–AF9 with Antisense Oligodeoxyribonucleotide Alters the Expression of HOX Genes and Induces Apoptosis in a Human Leukemia Cell LIne THP–1," Blood, 96 (11 Part 1): 303a(2000).
Shimada, H., et al., "Analysis of Genes Under the Downstream Control of the t(8;21) Fusion Protein AML1–MTG8: Overexpression of the TIS11b (EFR–I, cMG1) Gene Induces Myeloid Cell Proliferation in Response to G–CSF," Blood, 96:655–663 (2000).
Yuge, M., et al., "Comparison of MRNA Expression Patterns at Diagnosis and Relapse in Acute Lymphoblastic Leukemia by Differential Display Analysis," Blood, 96 (11 Part 2): 169b (2000).
Armstrong, S. A., et al., "MLL Translocations Specify a Distinct Gene Expression Profile that Distinguishes a Unique Leukemia," Nature Genetics, 30:41–47 (2002).
Armstrong, S. A., et al., "The Gene Expression Profile of Infant Acute Lymphoblastic Leukemia," Leukemia, 15 (2001). (Abstract No. 029).
Bavikatty, N.R., et al., "Anti–CD10 Immunoperoxidase Staining of Parrafin–Embedded Acute Leukemias: Comparison With Flow Cytometric Immunophenotyping," Human Pathology, 31:1051–1054 (2000).
Dong, W–F., et al., "Expression of Rhombotin 2 in Normal and Leukaemic Haemopoietic Cells," British Journal of Haematology, 93:280–286 (1996).
Dorsam, S., et al., "A Global Survey of Transcriptional Targets of the AML–Associated Homeobox Protein, HOXA9, Using cDNA Microarray Analysis," Blood, 98(11 Part 1):285A (2001). (Abstract No. 1203).
Ferrando, A. A., et al., "Prognostic Classification of Pediatric T–ALL Using Oligonucleotide Microarrays," Blood, 98(11 Part 1) :759A–760A (2001). (Abstract No. 3163).
Frank, K. M., et al., "Late Embryonic Lethality and Impaired V(D)J Recombination in Mice Lacking DNA ligase IV," Nature, 396:173–177 (1998).
Fruman, D. A., et al., "Impaired B Cell Development and Proliferation in Absence of Phosphoinositide 3–Kinase p85α," Science, 283:393–397 (1999).
Golub, T.R., et al., "Molecular Classification of Cancer: Class Discovery and Class Prediction by Gene Expression Monitoring," Science, 286:531–537 (1999).

(Continued)

Primary Examiner—David Guzu
Assistant Examiner—Michael D. Burkhart
(74) Attorney, Agent, or Firm—Fish & Neave IP Group, Ropes & Gray LLP

(57) ABSTRACT

The present invention relates to the diagnosis of mixed lineage leukemia (MLL), acute lymphoblastic leukemia (ALL), and acute myelogenous leukemia (AML) according to the gene expression profile of a sample from an individual, as well as to methods of therapy and screening that utilize the genes identified herein as targets.

7 Claims, 23 Drawing Sheets

OTHER PUBLICATIONS

Hardy, R. R., and Hayakawa, K., "B Cell Development Pathways," *Annual Review of Immunology*, 19:595–621 (2001).

Hattenhorst, U., et al., "Differential Gene Expression Analysis in Pediatric Common Acute Lymphoblastic Leukemia Versus Normal Pre–B–Cells and Bone Marrow Utilizing DNA–Microarrays," *Blood*, 96(11)(2000). (Abstract No. 458).

Hess, J. L., et al., "The Mixed–Lineage Leukemia Gene (*MLL*) is Required for Maintenance of HOX Gene Expression and for Normal Hematopoieses," *Blood*, 88(10) Supplement 1 (1996). (Abstract No. 179).

Ho, E. L., et al., "Murine *Nkg2d* and *Cd94* are Clustered Within the Natural Killer Complex and are Expressed Independently in Natural Killer Cells," *Proc. Natl. Acad. Sci. USA*, 95:6320–6325 (1998).

Kawagoe, L., et al., "Expression of HOXA9, A10 and MLL in Phenotypically and Functionally Defined Subpopulations of Leukemic and Normal Human Hematopoietic Cells," *Blood*, 90(10) Supplement 1 (1997) (Abstract No. 1447).

Kern, W., et al., "Correlation of Gene Expression and Protein Expression in Acute Myeloid Leukemia as Assessed by Microarray Analysis and Flow Cytometry," *Blood* 98(11):1–3 (2001) (Abstract No. 383).

Kondo, M., et al., "Identification of Clonogenic Common Lymphoid Progenitors in Mouse Bone Marrow," *Cell*, 91:661–672 (1997).

LeBien, T.W., "Fates of Human B–cell Precursors," *Blood*, 96(1):9–23 (2000).

Mills, K. I., et al., "Gene Array Chips for Defining Prognosis in Acute Myeloid Leukaemia: A Feasibility Study," *Blood*, 98(11 Part 1) (2001) (Abstract No. 379).

Murre, C., "Role of Helix–Loop–Helix Proteins in Lymphocyte Development." In *Cold Spring Harbor Symposia on Quantitative Biology*, vol. LXIV. (NY: Cold Spring Harbor Laboratory Press), pp. 39–44 (1999).

Nakamura T., et al., "Cooperative Activation of *Hoxa* and *Pbx1*–Related Genes in Murine Myeloid Leukemias," *Nature Genetics*, 12:149–153 (1996).

O'Neill, C. M., et al., "Differential Expression of Homeobox Genes in the Leukaemic Cell Line HL–60 Using Real Time Quantitative PCR," *British Journal of Haematology*, 113(Supplement 1):27 (2001). (Abstract No. 100).

Remold–O'Donnell, E., et al., "Sequence and Molecular Characterization of Human Monocyte/Neutrophil Elastase Inhibitor," *Proc. Natl. Acad. Sci. USA*, 89:5635–5639 (1992).

Rosenberg, H. F., et al., "Human Eosinophil Cationic Protein: Molecular Cloning of a Cytotoxin and Helminthotoxin with Ribonuclease Activity," *The Journal of Experimental Medicine*, 170:163–176 (1989).

Rosnet, O., et al., "Human *FLT3/FLK2* Gene: cDNA Cloning and Expression in Hematopoietic Cells," *Blood*, 82:1110–1119 (1993).

Rozovskaia, T., et al., "Upregulation of *Meis1* and *HoxA9* in Acute Lymphocytic Leukemias with the t(4:11) Abnormality," *Oncogene*, 20:874–878 (2001).

Schubart, K., et al., "B Cell Development and Immunoglobuline Gene Transcription in the Absence of Oct–2 and OBF–1," *Nature Immunology*, 2(1):69–74 (2001).

Thompson, A., et al., "Small Array Real Time (SMART) Quantitative PCR Profiling of Hox Genes in AML and All Patients," *British Journal of Haematology*, 113 (Supplement 1) (2001). (Abstract No. 103).

Thompson, A., et al., "Smart Quantitative PCR Profiling of Hox Gene Expression: Application to Pathogenesis and Treatment Monitoring of Leukemia," *Blood*, 96(11)(2000). (Abstract No. 1342).

Yang, R., et al., "Cyclin A1 Expression in Leukemia and Normal Hematopoietic Cells," *Blood*, 93:2067–2074 (1999).

Yeoh, E.–J., et al., "Expression Profiling of Pediatric Acute Lymphoblastic Leukemia (ALL) Blasts at Diagnosis Accurately Predicts Both the Risk of Relapse and of Developing Therapy–Induced Acute Myeloid Leukemia (AML)," *Blood* 98 (11 Part 1):(2001) (Abstract No. 1816).

Yin, A. H., et al., "AC133, a Novel Marker for Human Hematopoietic Stem and Progenitor Cells," *Blood*, 90:5002–5012 (1997).

Yu, B. D., et al., "Altered *Hox* Expression and Segmental Identity in *Mll*–Mutant Mice," *Nature*, 378:505–508 (1995).

* cited by examiner

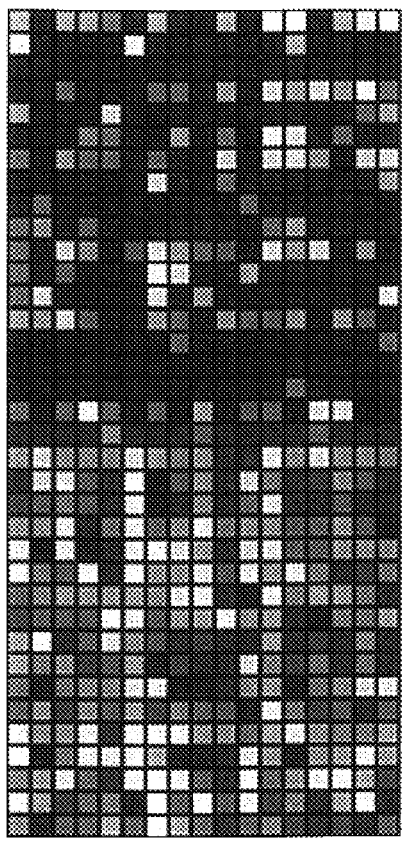

| | |
|---|---|
| D87437 | KIAA0250 |
| Y00264 | APP (Amyloid A4) |
| U59912 | MADH1 (Smad1) |
| AJ007583 | LARGE (Glycosytransferase) |
| L75847 | ZNF45 |
| D17530 | DBN1 (Drebrin E) |
| D86967 | KIAA0212 |
| J03600 | ALOX5 (Lipoxygenase) |
| D42055 | KIAA0212 |
| AL021154 | Chromosome 1 PAC |
| AI761647 | cDNA mg66h09 |
| AF054825 | VAMP5 |
| N36926 | cDNA YY38E04 |
| U96113 | NEDD4L (Ubiquitin ligase) |
| AB019527 | LDOC1 |
| M34641 | FGFR1 |
| L29376 | MHC class 1 mRNA |
| M60028 | HLA-DQB1 |
| AI535946 | LGALS1 (Galectin-1) |
| M14087 | LGALS1 (Galectin-1) |
| AI201310 | cDNAqf7b11 |
| M80899 | AHNAK |
| AJ001687 | NKG2D |
| U66838 | CCNA1 (Cyclin A1) |
| M59040 | CD44 |
| M95929 | PMX1 (PHOX1) |
| D25217 | KIAA0027 |
| AI597616 | cDNAtn15f08 |
| W72186 | cDNAzd69b10 |
| U41813 | HOXA9 |
| L05424 | CD44 |
| L05424 | CD44 |
| AC004080 | Chromosome 7 clone |
| X05908 | ANXA1 (Annexin 1) |
| U78027 | Chromosome X clone |
| Y00062 | PTPRC (CD45) |

FIG. 1D

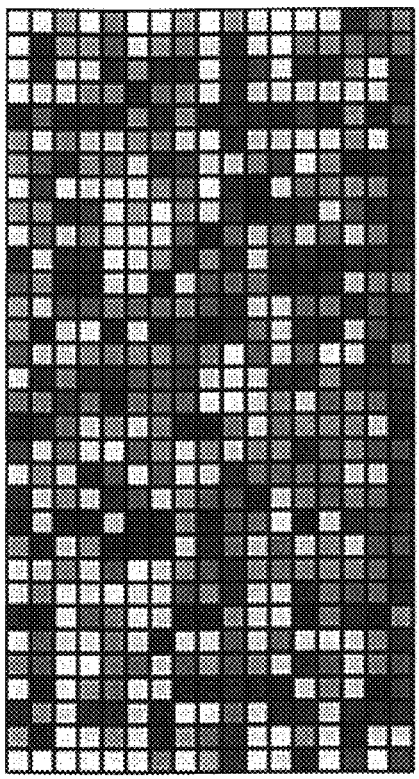

| | |
|---|---|
| AF098641 | CD44 |
| Y00638 | PTPRC (CD45) |
| AF004230 | LILRB1 |
| W60864 | cDNAzd27g05 |
| X55989 | RNASE3 (Eosinophil-CRP) |
| M93058 | SERPINB1 (Monocyte elastase inhibitor) |
| AF027208 | PROML1 (AC133) |
| Z83844 | Chromosome 22 sequence |
| AL050396 | DKFZp586K1720 |
| AA978353 | cDNAog40b07 |
| D21261 | KIAA0120 |
| L08177 | EB12 |
| L19182 | IGFBP7 (MAC25) |
| D28364 | ANXA2 (Annexin 11) |
| D15057 | DAD1 |
| AF020044 | SCGF |
| AI138834 | cDNAqe04b02 |
| X73882 | MAP7 |
| AF026816 | ITPA (Inosine triphosphatase) |
| X17042 | PRG1 (Proteogylcan 1) |
| M20867 | GLUD1 (Glutamate dehydrogenase) |
| U60060 | FEZ1 |
| AF025529 | ULRA1 |
| AB007888 | KIAA0428 |
| M13485 | MT1B (Metallothionein 1B) |
| M26679 | HOXA5 |
| AL050267 | DKFZp564A032 |
| R92331 | cDNA03h03 |
| AL050162 | DKFZp586B2022 |
| AJ017574 | cDNAou23f10 |
| M62898 | ANXA2P2 |
| AL050374 | DKFZp586c1619 |

FIG. 1F

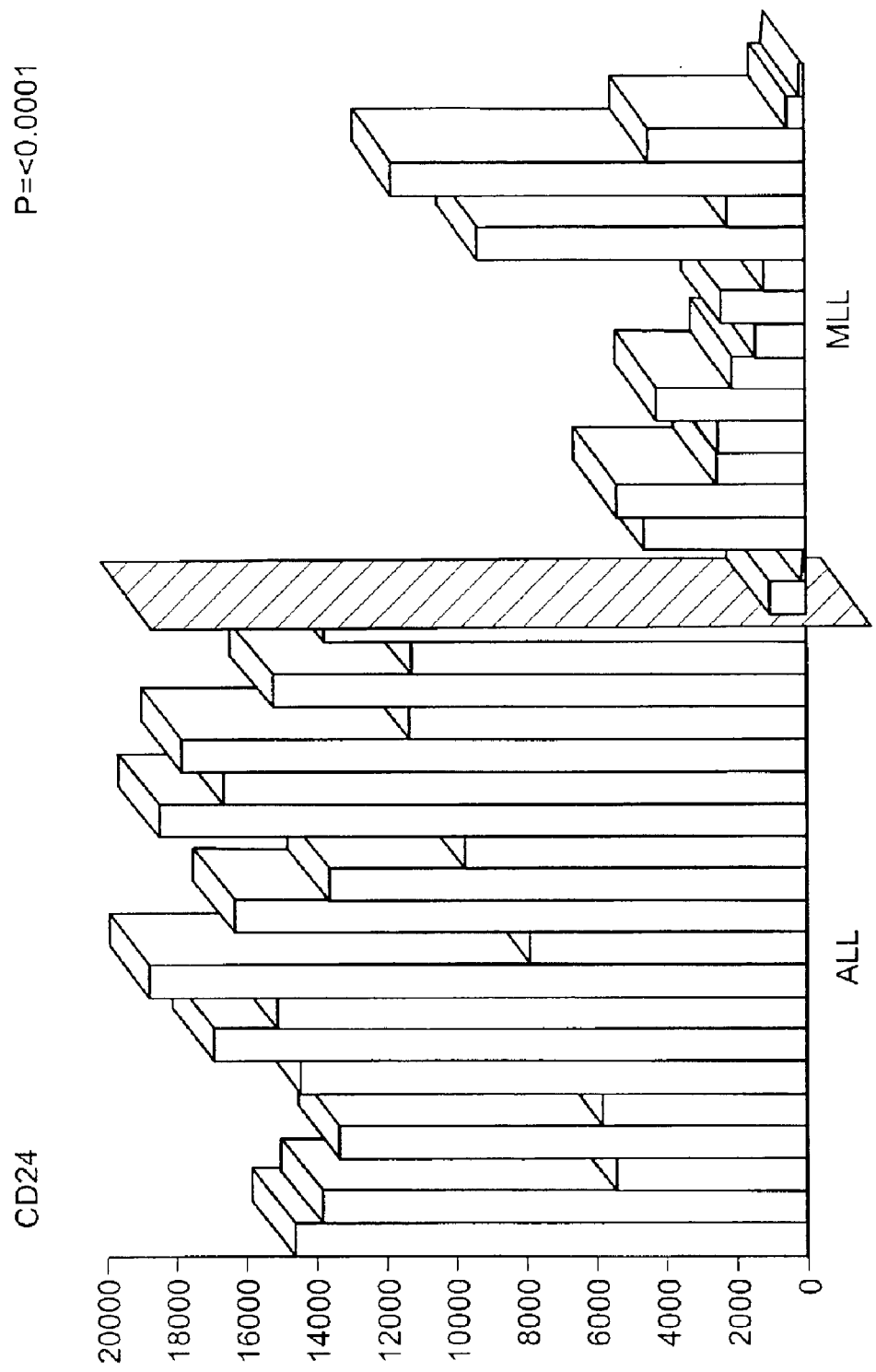

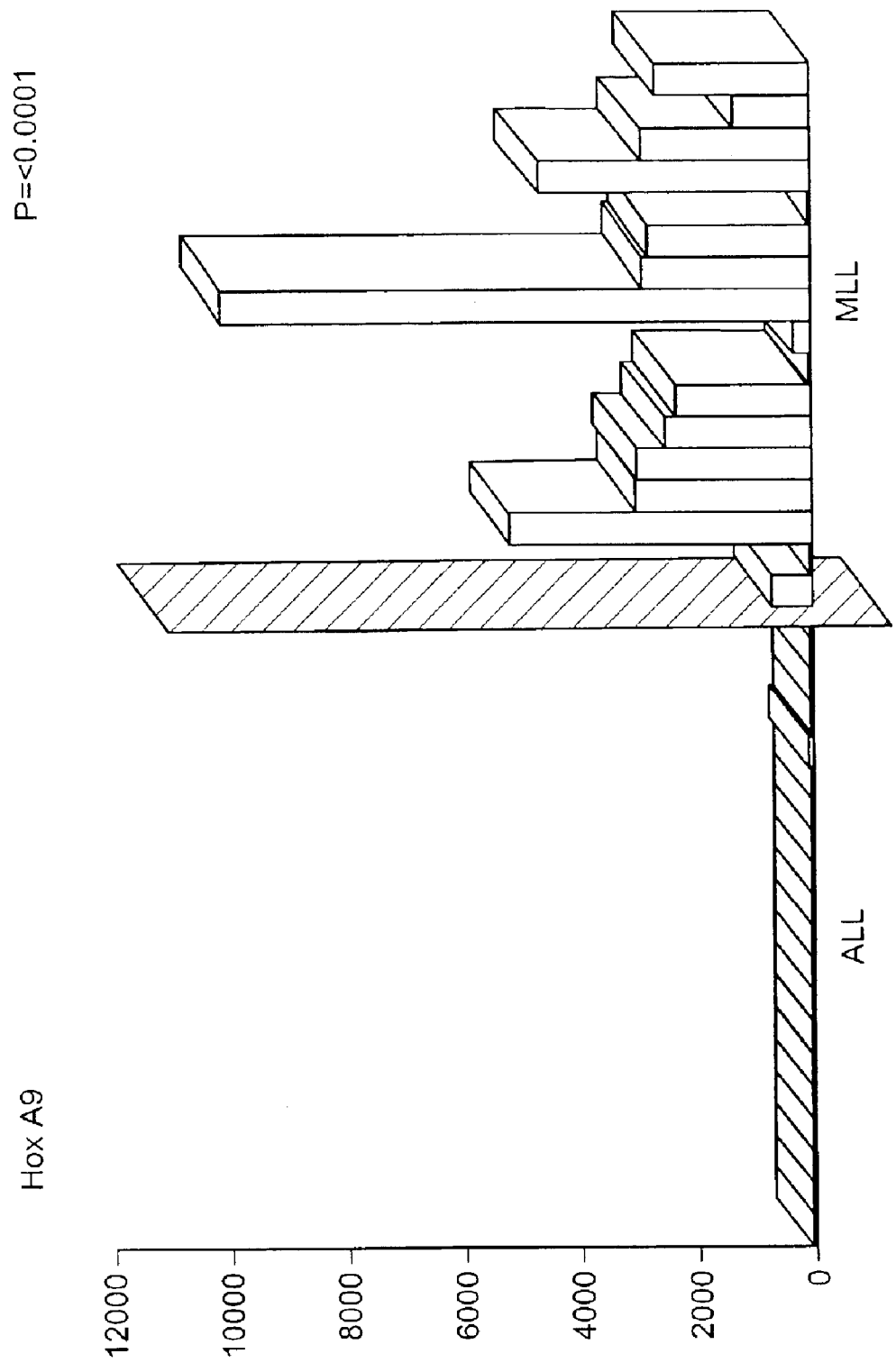

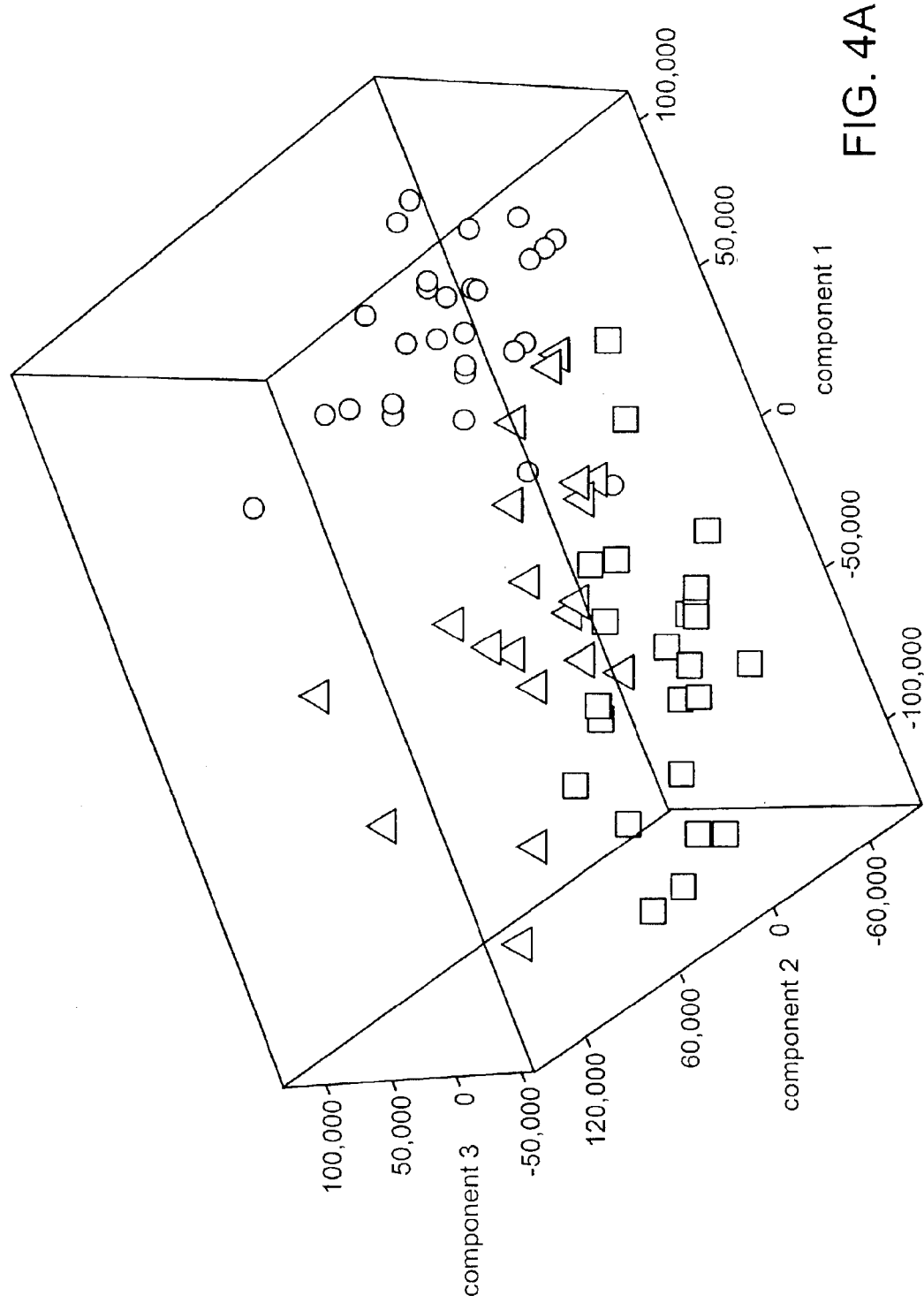

MLL TRANSLOCATIONS SPECIFY A DISTINCT GENE EXPRESSION PROFILE, DISTINGUISHING A UNIQUE LEUKEMIA

RELATED APPLICATIONS

This application claims the benefit of U.S. Provisional Application No. 60/306,103 filed on Jul. 17, 2001. The entire teachings of the above application are incorporated herein by reference.

GOVERNMENT SUPPORT

The invention was supported, in whole or in part, by a grant P01CA68484 from the National Institutes of Health. The Government has certain rights in the invention.

BACKGROUND OF THE INVENTION

A subset of human acute leukemias with a decidedly unfavorable prognosis possess a chromosomal translocation involving the Mixed Lineage Leukemia (MLL, HRX, AU-1) gene on chromosome segment 11q23. The leukemic cells, which typically have a lymphoblastic morphology, have been classified as Acute Lymphoblastic Leukemia (ALL). However, unlike the majority of childhood ALL, the presence of the MLL translocations often results in an early relapse after chemotherapy. As MLL translocations are typically found in leukemias of infants and chemotherapy-induced leukemia, it has remained uncertain whether host related factors or tumor-intrinsic biological differences are responsible for the poor survival in patients with the translocations. Lymphoblastic leukemias with either rearranged or germline MLL are similar with respect to most morphological and histochemical characteristics. Immunophenotypic differences associated with lymphoblasts bearing an MLL translocation include the lack of the early lymphocyte antigen CD 10, expression of the proteoglycan NG2, and the propensity to co-express the myeloid antigens CD15 and CD65. This prompted the corresponding disease to be called Mixed Lineage Leukemia and suggested models, largely unresolved, in which the leukemia reflects disordered cell fate decisions or the transformation of a more multi-potential progenitor.

Generally, therapeutic treatment is more successful when tailored to the specific type of leukemia. Thus, a need exists for accurate and efficient methods for diagnosis of leukemia and identification of subclasses of leukemias.

SUMMARY OF THE INVENTION

As described herein, MLL is significantly different from ALL and AML, as assessed by gene expression profiling. The expression profiles reported here reveal that lymphoblastic leukemias bearing MLL translocations display a remarkably uniform and highly distinct pattern that clearly distinguishes them from conventional ALL or AML and warrants designation as a distinct disease, MLL.

In one embodiment, the invention relates to a method of diagnosing mixed lineage leukemia, acute lymphoblastic leukemia or acute myelogenous leukemia, comprising determining a gene expression profile of a gene expression product from at least one informative gene from one or more cells, wherein the cells are selected from the group consisting of mononuclear blood cells and bone marrow cells, and wherein the gene expression profile is correlated with mixed lineage leukemia, acute lymphoblastie leukemia or acute myelogenous leukemia. In one embodiment, the gene expression product is RNA. In a preferred embodiment, the gene expression profile is determined utilizing specific hybridization probes. In a particularly preferred embodiment, the gene expression profile is determined utilizing oligonucleotide microarrays. In a preferred embodiment, the gene expression profile is determined utilizing antibodies. In particular embodiments, the informative gene(s) is selected from the group consisting of the genes in FIGS. 1A–1F, 2A–2F, 3A–3D, and 5A–5D, and Tables 1 and 2.

The invention further relates to a method of diagnosing mixed lineage leukemia, acute lymphoblastic leukemia or acute myelogenous leukemia, comprising determining a gene expression profile of mRNA from at least one informative gene, wherein the mRNA is isolated from one or more cells of an individual selected from the group consisting of mononuclear blood cells and bone marrow cells; and comparing the obtained gene expression profile to a gene expression profile of a control sample selected from the group consisting of a mixed lineage leukemia sample, an acute lymphoblastic leukemia sample and an acute myelogenous leukemia sample, wherein the gene expression profile of the cell from the individual is indicative of mixed lineage leukemia, acute lymphoblastic leukemia or acute myelogenous leukemia.

The invention also relates to a method of diagnosing mixed lineage leukemia, comprising determining a gene expression profile of a gene expression product from at least one informative gene from one or more cells selected from the group consisting of mononuclear cells and bone marrow cells, wherein the gene expression profile is correlated with mixed lineage leukemia.

The invention further relates to a method of identifying a compound for use in treating mixed lineage leukemia, acute lymphoblastic leukemia, or acute myelogenous leukemia, comprising determining a gene expression profile of a gene expression product from at least one informative gene from one or more cells selected from the group consisting of mononuclear blood cells and bone marrow cells of an individual with mixed lineage leukemia, acute lymphoblastic leukemia, or acute myelogenous leukemia; administering a test agent to the individual; determining a gene expression profile of a gene expression product from at least one informative gene from one or more cells selected from the group consisting of mononuclear blood cells and bone marrow cells from the individual; and comparing the two gene expression profiles, wherein if the gene expression profile from the individual after administration of the agent is correlated with effective treatment of mixed lineage leukemia, acute lymphoblastic leukemia, or acute myelogenous leukemia, the test agent is a therapeutic agent. In one embodiment, the disease is mixed lineage leukemia, and a decrease in the expression of the informative gene selected from the group consisting of FLT3, MEIS1, and HoxA9, is indicative of effective treatment of mixed lineage leukemia. In another embodiment, the gene expression profiles compared prior to and after administration of the test agent consist of one or more of the same informative genes.

The invention also relates to a method for evaluating drug candidates for their effectiveness in treating mixed lineage leukemia, acute lymphoblastic leukemia, or acute myelogenous leukemia, comprising contacting a cell sample or lysate thereof with a candidate compound, wherein the cell is selected from the group consisting of mononuclear blood cells and bone marrow cells; and detecting an alteration of a gene expression profile of a gene expression product from at least one informative gene from the cell sample or lysate thereof, wherein a compound that increases the gene expression profile of at least one informative gene which is decreased in mixed lineage leukemia, acute lymphoblastic leukemia, or acute myelogenous leukemia is a compound for use in treating mixed lineage leukemia, acute lymphoblastic leukemia, or acute myelogenous leukemia.

The invention further relates to a method of identifying a compound for use in treating mixed lineage leukemia, acute lymphoblastic leukemia, or acute myelogenous leukemia, comprising contacting a cell sample or lysate thereof with a candidate compound, wherein the cell is selected from the group consisting of mononuclear blood cells and bone marrow cells; and detecting an alteration of a gene expression profile of a gene expression product from at least one informative gene from the cell sample or lysate thereof, wherein a compound that decreases the gene expression profile of at least one informative gene which is increased in mixed lineage leukemia, acute lymphoblastic leukemia, or acute myelogenous leukemia is a compound for use in treatingmixed lineage leukemia, acute lymphoblastic leukemia, or acute myelogenous leukemia.

The invention further relates to a method of identifying a compound for use in treating mixed lineage leukemia, acute lymphoblastic leukemia, or acute myelogenous leukemia, comprising contacting a cell sample or lysate thereof with a candidate compound, wherein the cell is selected from the group consisting of mononuclear blood cells and bone marrow cells; and detecting an alteration of a gene expression profile of a gene expression product from at least one informative gene from the cell sample or lysate thereof, wherein a compound that increases the gene expression profile of at least one informative gene which is decreased in mixed lineage leukemia, acute lymphoblastic leukemia, or acute myelogenous leukemia is a compound for use in treating acute lymphoblastic leukemia. In a preferred embodiment, the disease is mixed lineage leukemia, and the informative gene is selected from the group consisting of FLT3, MEIS1, and HoxA9.

In another aspect, the invention relates to a method of identifying a compound that modulates (increases or decreases) the biological activity of an informative gene.

In still another aspect, the invention features a metho of identifying a compound that decreases the biological activity of an informative gene expression product having increased expression in MLL, AML, or ALL. The method comprises contacting the informative gene expression product with a candidate compound under conditions suitable for activity of the informative gene expression product; and assessing the biological activity level of the informative gene expression product. A candidate compound that decreases the biological activity level of the informative gene expression product relative to a control is a compound that decreases the biological activity of the informative gene expression product having increased expression in MLL, AML, or ALL. In one embodiment, the method is carried out in a cell or animal. In another embodiment, the method is carried out in a cell-free system. In still another embodiment the informative gene expression product is selected from the gene expression products encoded by the genes in FIGS. 1A–1F, 2A–2F, 3A–3D, and 5A–5D, and Tables 1 and 2.

In another aspect, the invention features a method of identifying a compound that increses the biological activity of an informative gene expression product having decreased expression in MLL, AML, or ALL. The method comprises contacting the informative gene expression product with a candidate compound under conditions suitable for biological activity of the informative gene expression product; and assessing the biological activity level of the informative gene expression product. A candidate compound that increases the biological activity level of the informative gene expression product relative to a control is a compound that increases the biological activity of the informative gene expression product having decreased expression in MLL, AML, or ALL. In one embodiment, the method is carried out in a cell or animal. In another embodiment, the method is carried out in a cell-free system. In still another embodiment the informative gene expression product is selected from the gene expression products encoded by the genes in FIGS. 1A–1F, 2A–2F, 3A–3D, and 5–5D, and Tables 1 and 2.

In other embodiments, screens can be carried out for compounds that further increase the expression of a gene or the biological activity of a gene expression product already overexpressed in MLL, ALL, or AML, or that further decrease the expression of a gene or the biological activity of a gene expression product already underexpressed in MLL, ALL, or AML. These compounds can be identified according the screening methods described herein. These compounds should be avoided during treatment regimens for MLL, ALL, or AML.

In still another aspect, the invention features a method of identifying a polypeptide that interacts with an informative gene expression product having increased or decreased expression in MLL, AML or ALL in a yeast two-hybrid system. The method comprises providing a first nucleic acid vector comprising a nucleic acid molecule encoding a DNA binding domain and a polypeptide encoded by the informative gene that is increased or decreased in MLL, AML, or ALL; providing a second nucleic acid vector comprising a nucleic acid encoding a transcription activation domain and a nucleic acid encoding a test polypeptide; contacting the first nucleic acid vector with the second nucleic acid vector in a yeast two-hybrid system; and assessing transcriptional activation in the yeast two-hybrid system. An increase in transcriptional activation relative to a control indicates that the test polypeptide is a polypeptide that interacts with the informative gene expression product having increased or decreased expression in MLL, AML or ALL.

The invention also relates to compounds identified according to the above-described screening methods. Such compounds can be used to treat mixed lineage leukemia, acute lymphoblastic leukemia, or acute myelogenous leukemia, as appropriate.

The invention further relates to a method for evaluating a drug candidate for effectiveness in treating mixed lineage leukemia, acute lymphoblastic leukemia, or acute myelogenous leukemia, comprising determining a gene expression profile of a gene expression product from at least one informative gene, wherein the gene expression product is isolated from cells derived from a blood or bone marrow sample from an individual to whom the drug candidate has been administered, wherein the gene expression profile is indicative of the effectiveness of the drug candidate in treating mixed lineage leukemia, acute lymphoblastic leukemia, or acute myelogenous leukemia.

The invention also relates to a method for monitoring the efficacy of a mixed lineage leukemia, acute lymphoblastic leukemia, or acute myelogenous leukemia treatment, comprising determining the gene expression profile a gene expression product from at least one informative gene in a cell from blood samples derived from an individual being treated, wherein the samples are obtained at various time points; and comparing the treatment outcome of the samples at various times during treatment, wherein the efficacy of mixed lineage leukemia, acute lymphoblastic leukemia, or acute myelogenous leukemia treatment is determined. In one embodiment the gene expression profiles obtained over time is compared to gene expression profiles from individuals who do not have MLL, ALL, or AML (normal individuals). In another embodiment, the gene expression profiles determined at various time points include one or more of the same informative genes.

The invention also encompasses a method of predicting the efficacy of treating mixed lineage leukemia, acute lymphoblastic leukemia, or acute myelogenous leukemia, comprising determining a gene expression profile of a gene expression product from at least one informative gene, the gene expression product isolated from one or more cells selected from the group consisting of mononuclear cells and bone marrow cells of an individual with mixed lineage leukemia, acute lymphoblastic leukemia, or acute myelogenous leukemia, wherein the gene expression profile is correlated with a treatment outcome. In one embodiment the gene expression profiles obtained is compared to gene expression profiles from individuals who do not have MLL, ALL, or AML (normal individuals)

The invention also relates to a method of treating mixed lineage leukemia, comprising administering to an individual in need thereof a therapeutic amount of an agent that inhibits the activity of a gene product that is increased in mixed lineage leukemia. In a preferred embodiment, gene product is encoded by an informative gene selected from the group consisting of FLT3, MEIS1, and HoxA9.

The invention further relates to a method of treating mixed lineage leukemia, comprising administering to an individual in need thereof a therapeutic amount of an agent which enhances the activity of a gene product which is decreased in mixed lineage leukemia.

In any of the above methods, the gene expression product may be RNA and the gene expression profile can be determined utilizing specific hybridization probes. In a particularly preferred embodiment, the gene expression profile is determined utilizing oligonuclcetide microarrays. In another preferred embodiment, the gene expression profile is determined utilizing antibodies. In particular embodiments, the informative gene(s) is selected from the group consisting of the genes in FIGS. 1A–1F, 2A–2F, 3A–3D, and 5A–5D, and Tables 1 and 2.

The invention also relates to an oligonucleotide microarray having immobilized thereon a plurality of oligonucleotide probes specific for one or more informative genes for diagnosing mixed lineage leukemia, acute lymphoblastic leukemia, or acute myelogenous leukemia wherein the informative genes are selected from the group consisting of the genes in FIGS. 1A–1F, 2A–2F, 3A–3D, and 5A–5D, and Tables 1 and 2.

It is well known that proper diagnosis of disease is essential for successful treatment of individuals. The present invention will significantly improve the diagnosis of MLL, ALL, and ALL, and thereby improve the treatment of leukemic individuals.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 1 provides a key depicting how FIGS. 1A–1F are assembled to produce a complete figure.

FIG. 1A, when assembled with FIGS. 1B–1F as shown in FIG. 1, illustrates genes that distinguish ALL (left-most 20 columns of assembled FIG. 1) from MLL (right-most 17 columns of assembled FIG. 1). The 100 genes most highly correlated with the class distinction are shown. Each column represents a leukemia sample and each row represents an individual gene. Expression levels are normalized for each gene where the mean is 0. Expression levels greater than the mean are shown in red, whereas levels less than the mean are shown in blue. Increasing distance from the mean is represented by increasing color intensity.

FIG. 1B, when assembled with FIGS. 1A and 1C–1F as shown in FIG. 1, illustrates genes that distinguish ALL (left-most 20 columns of assembled FIG. 1) from MLL (right-most 17 columns of assembled FIG. 1). The 100 genes most highly correlated with the class distinction are shown. Each column represents a leukemia sample and each row represents an individual gene. Expression levels are normalized for each gene where the mean is 0. Expression levels greater than the mean are shown in red, whereas levels less than the mean are shown in blue. Increasing distance from the mean is represented by increasing color intensity.

FIG. 1C, when assembled with FIGS. 1A, 1B and 1D–1F illustrates genes that distinguish ALL (left-most 20 columns of assembled FIG. 1) from MLL (right-most 17 columns of assembled FIG. 1). The 100 genes most highly correlated with the class distinction are shown. Each column represents a leukemia sample and each row represents an individual gene. Expression levels are normalized for each gene where the mean is 0. Expression levels greater than the mean are shown in red, whereas levels less than the mean are shown in blue. Increasing distance from the mean is represented by increasing color intensity.

FIG. 1D, when assembled with FIGS. 1A–1C, 1E and 1F illustrates genes that distinguish ALL (left-most 20 columns of assembled FIG. 1) from MLL (right-most 17 columns of assembled FIG. 1). The 100 genes most highly correlated with the class distinction are shown. Each column represents a leukemia sample and each row represents an individual gene. Expression levels are normalized for each gene where the mean is 0. Expression levels greater than the mean are shown in red, whereas levels less than the mean are shown in blue. Increasing distance from the mean is represented by increasing color intensity.

FIG. 1E, when assembled with FIGS. 1A–1D and 1F illustrates genes that distinguish ALL (left-most 20 columns of assembled FIG. 1) from MLL (right-most 17 columns of assembled FIG. 1). The 100 genes most highly correlated with the class distinction are shown. Each column represents a leukemia sample and each row represents an individual gene. Expression levels are normalized for each gene where the mean is 0. Expression levels greater than the mean are shown in red, whereas levels less than the mean are shown in blue. Increasing distance from the mean is represented by increasing color intensity.

FIG. 1F, when assembled with FIGS. 1A–1E illustrates genes that distinguish ALL (left-most 20 columns of assembled FIG. 1) from MLL (right-most 17 columns of assembled FIG. 1). The 100 genes most highly correlated with the class distinction are shown. Each column represents a leukemia sample and each row represents an individual gene. Expression levels are normalized for each gene where the mean is 0. Expression levels greater than the mean are shown in red, whereas levels less than the mean are shown in blue. Increasing distance from the mean is represented by increasing color intensity.

FIG. 2D illustrates selected early lymphocyte gene expression in ALL and MLL. Relative levels of expression of CD24 in ALL and MLL samples are shown. Each bar represents an individual leukemia sample. The expression values are raw data obtained from Affymetrix GENECHIP® analysis after scaling of the arrays based on the scaling described in the Examples.

FIG. 3A illustrates selected HOXA9 gene expression in ALL and MLL. Relative levels of expression of HOXA9 in ALL and MLL samples are shown. The expression values are obtained using Affymetrix GENECHIP® analysis after scaling of the arrays as described in the Examples.

FIG. 4A illustrates the comparison of gene expression between ALL, MLL and AML, and shows the principal component analysis (PCA) plot of ALL (squares), MLL (triangles), and AML (circles) performed using 8700 genes that passed filtering.

FIG. 5A, when assembled with FIGS. 5B–5D as shown in FIG. 5, illustrates genes specifically expressed in MLL, ALL or AML. The top 15 genes, and their corresponding GenBank Accession Numbers, that are most highly correlated with one type of leukemia versus the other two are shown. Each column represents a leukemia sample and each row a gene. The relative levels of expression are shown in red (relatively high) and blue (relatively low) as described in FIGS. 1A–1F.

FIG. 5B, when assembled with FIGS. 5A, 5C and 5D as shown in FIG. 5, illustrates genes specifically expressed in MLL, ALL or AML. The top 15 genes, and their corresponding GenBank Accession Numbers, that are most highly correlated with one type of leukemia versus the other two are shown. Each column represents a leukemia sample and each row a gene. The relative levels of expression are shown in red (relatively high) and blue (relatively low) as described in FIGS. 1A–1F.

FIG. 5C, when assembled with FIGS. 5A, 5B and 5D as shown in FIG. 5, illustrates genes specifically expressed in MLL, ALL or AML. The top 15 genes, and their corresponding GenBank Accession Numbers, that are most highly correlated with one type of leukemia versus the other two are shown. Each column represents a leukemia sample and each row a gene. The relative levels of expression are shown in red (relatively high) and blue (relatively low) as described in FIGS. 1A–1F.

FIG. 5D, when assembled with FIGS. 5A, 5B and 5C as shown in FIG. 5, illustrates genes specifically expressed in MLL, ALL or AML. The top 15 genes, and their corresponding GenBank Accession Numbers, that are most highly correlated with one type of leukemia versus the other two are shown. Each column represents a leukemia sample and each row a gene. The relative levels of expression are shown in red (relatively high) and blue (relatively low) as described in FIGS. 1A–1F.

DETAILED DESCRIPTION OF THE INVENTION

Figure 1A:
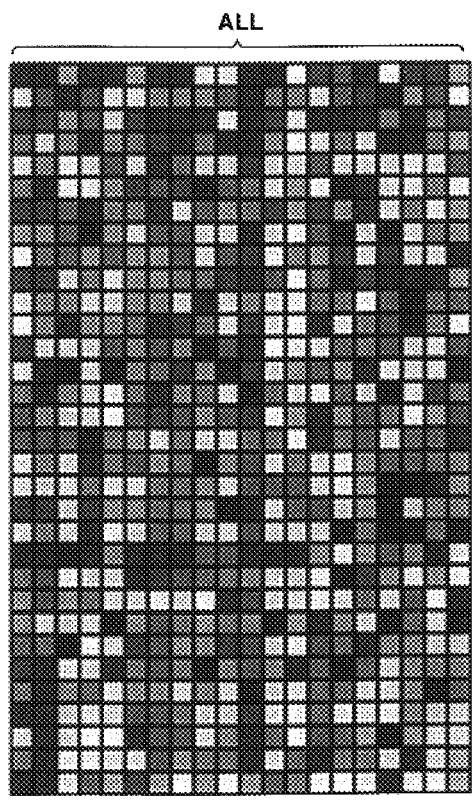

Early and accurate diagnosis of disease is of paramount importance in rendering effective treatment. The present invention relates to the diagnosis of mixed lineage leukemia (MLL), acute lymphoblastic leukemia (ALL), and acute myelogenous leukemia (AML) according to the gene expression profile of a sample from an individual, as well as to methods of therapy and screening that utilize the genes identified herein as targets.

In one embodiment, the present invention is directed to a method of diagnosing mixed lineage leukemia, acute lymphoblastic leukemia and acute myelogenous leukemia, comprising isolating a gene expression product from at least one informative gene from one or more cells of an individual selected from the group consisting of mononuclear blood cells and bone marrow cells; and determining a gene expression profile of at least one informative gene, wherein the gene expression profile is correlated with mixed lineage leukemia, acute lymphoblastic leukemia and acute myelogenous leukemia.

In another embodiment, the present invention is directed toward a method of diagnosing mixed lineage leukemia, acute lymphoblastic leukemia and acute myelogenous leukemia, comprising isolating mRNA from one or more cells of an individual, wherein the cells are selected from the group consisting of mononuclear blood cells and bone marrow cells, determining a gene expression profile of at least one informative gene, and comparing the gene expression profile with a gene expression profile of a control sample selected from the group consisting of mixed lineage leukemia sample, acute lymphoblastic leukemia sample and acute myelogenous leukemia sample, wherein the gene expression profile obtained from the cells of the individual is indicative of mixed lineage leukemia, acute lymphoblastic leukemia or acute myelogenous leukemia.

In one example of the above method, if the gene expression product obtained from the sample is similar to the gene expression product of MLL, then the individual is diagnosed as having MLL; and if the gene expression product obtained from the sample is similar to the gene expression product of ALL, then the individual is diagnosed as having ALL; and if the gene expression product obtained from the sample is similar to the gene expression product of AML, then the individual is diagnosed as having AML. Using similar methods, the diagnosis of certain types of leukemias (MLL, ALL, or AML) can also be ruled out.

"Gene expression profile" as used herein is defined as the level or amount of gene expression of particular genes as assessed by methods described herein. The gene expression profile can comprise data for one or more genes and can be measured at a single time point or over a period of time.

As used herein, "gene expression products" are proteins, polypeptides, or nucleic acid molecules (e.g., mRNA, tRNA, rRNA, or cRNA) that result from transcription or translation of genes. The present invention can be effectively used to analyze proteins, peptides or nucleic acid molecules that are the result of transcription or translation. The nucleic acid molecule levels measured can be derived directly from the gene or, alternatively, from a corresponding regulatory gene or regulatory sequence element. All forms of gene expression products can be measured. Additionally, variants of genes and gene expression products including, for example, spliced variants and polymorphic alleles, can be measured. Similarly, gene expression can be measured by assessing the level of protein or derivative thereof translated from mRNA. The sample to be assessed can be any sample that contains a gene expression product. Suitable sources of gene expression products, e.g., samples, can include intact cells, lysed cells, cellular material for determining gene expression, or material containing gene expression products. Examples of such samples are brain, blood, bone marrow, plasma, lymph, urine, tissue, mucus, sputum, saliva or other cell samples. Methods of obtaining such samples are known in the art. In a preferred embodiment, mononuclear bloods cells are used. In another preferred embodiment, bone marrow tissue is used.

In one embodiment, the gene expression product is a protein or polypeptide. In this embodiment the determination of the gene expression profile can be made using techniques for protein detection and quantitation known in the art. For example, antibodies specific for the protein or polypeptide can be obtained using methods which are routine in the art, and the specific binding of such antibodies to protein or polypeptide gene expression products can be detected and measured.

The present invention also provides methods for classifying the sample. A sample can be classified in many ways including but not limited to leukemia subclass (e.g., ALL, AML, or MLL), response to a particular treatment, referred to herein as treatment outcome, or treatment efficacy. Informative genes include, but are not limited to, those shown in FIGS. 1A–1F, 2A–2F 3A–3D, and 5A–5D, and Tables 1 and 2. Using the methods described herein, expression of numerous genes can be measured simultaneously. The assessment of numerous genes provides for a more accurate evaluation of the sample because there are more genes that can assist in classifying the sample.

In a preferred embodiment, the gene expression product is mRNA and the gene expression levels are obtained, e.g., by contacting the sample with a suitable microarray, and determining the extent of hybridization of the nucleic acid in the sample to the probes on the microarray.

The gene expression value measured or assessed is the numeric value obtained from an apparatus that can measure gene expression levels. Gene expression levels refer to the amount of expression of the gene expression product, as described herein. The values are raw values from the apparatus, or values that are optionally rescaled, filtered and/or normalized. Such data is obtained, for example, from a GeneChip® probe array or Microarray (Affymetrix, Inc.) (U.S. Pat. Nos. 5,631,734, 5,874,219, 5,861,242, 5,858,659, 5,856,174, 5,843,655, 5,837,832, 5,834,758, 5,770,722, 5,770,456, 5,733,729, 5,556,752, all of which are incorporated herein by reference in their entirety), and the expression levels are calculated with software (e.g., Affymetrix GENECHIP® software). Nucleic acids (e.g., mRNA) from a sample which has been subjected to particular stringency conditions hybridize to the probes on the chip. The nucleic acid to be analyzed (e.g., the target) is isolated, amplified and labeled with a detectable label, (e.g., $^{32}P$ or fluorescent label) prior to hybridization to the arrays. Once hybridization occurs, the arrays are inserted into a scanner which can detect patterns of hybridization. The hybridization data are collected as light emitted from the labeled groups which is now bound to the probe array. The probes that perfectly match the target produce a stronger signal than those that have mismatches. Since the sequence and position of each probe on the array are known, by complementarity, the identity of the target nucleic acid applied to the probe is determined. Quantitation of gene profiles from the hybridization of labeled mRNA/DNA microarray can be performed by scanning the microarrays to measure the amount of hybridization at each position on the microarray with an Affymetrix scanner (Affymetrix, Santa Clara, Calif.). For each stimulus a time series of mRNA levels (C={$C_1,C_2,C_3,\ldots C_n$}) and a corresponding time series of mRNA levels (M={$M_1,M_2,M_3,\ldots M_n$}) in control medium in the same experiment as the stimulus is obtained. Quantitative data is then analyzed. $C_i$ and $M_i$ are defined as relative steady-state mRNA levels, where i refers to the ith timepoint and n to the total number of timepoints of the entire timecourse. $\mu M$ and $\sigma M$ are defined as the mean and standard deviation of the control time course, respectively. Microarrays are only one method of obtaining gene expression values. Other methods for obtaining gene expression values known in the art or developed in the future can be used with the present invention.

Once the gene expression values are prepared, the sample can be classified. Genes that are particularly relevant for classification have been identified as a result of work described herein and are shown in FIGS. 1A–1F, 2A–2F, 3A–3D, and 5A–5D, and Tables 1 and 2. The genes that are relevant for classification are referred to herein as "informative genes". Not all informative genes for a particular class distinction must be assessed in order to classify a sample. For example, a subset of the informative genes which demonstrate a high correlation with a class distinction can be used. This subset can be, for example, one or more genes, for example 2, 3, or 4 genes, 5 or more genes, for example 6, 7, 8, or 9 genes, 10 or more genes, 25 or more genes, 45 or more genes, or 50 or more genes. Typically the accuracy of the classification will increase with the number of informative genes assessed.

The correlation between gen expression profiles and class distinction can be determined using a variety of methods. Methods of defining classes and classifying samples are described, for example, in U.S. patent application Ser. No. 09/544,627, filed Apr. 6, 200 by Golub et al., the teachings of which are incorporated herein by reference in their entirety. The information provided by the present invention, alone or in conjunction with other test results, aids in sample classification and diagnosis of disease.

The present invention also provides methods for monitoring the effect of a treatment regimen in an individual by monitoring the gene expression profile for one or more informative genes. Treatment efficacy classification can be made by comparing the gene expression profile of a sample at several time points during treatment with respect to one or more informative genes. A treatment can be considered efficacious if the gene expression profile with regard to one or more informative genes tends toward a normal gene expression profile. That is, for example, treatment can be considered efficacious if a gene having increased expression in a disorder (e.g., MLL) shows reduced expression (i.e. expression tending toward normal expression) as a result of treatment. For example, in one method, a baseline gene expression profile for the individual can be determined, and repeated gene expression profiles can be determined at time points during treatment. A shift in gene expression profile from a profile correlated with poor treatment outcome to profile correlated with improved treatment outcome is evidence of an effective therapeutic regimen, while a repeated profile correlated with poor treatment outcome is evidence of an ineffective therapeutic regimen. For example, HOXA9 and MEISI upregulation has been correlated with a poor prognosis. An effective therapeutic regimen might be expected to reduce the level of HOXA9 and MEISI expression. Similarly, as described herein, expression of FLT3 is correlated with MLL. Thus, a reduction in the baseline level of FLT3 or its kinase activity can be indicative of an effective therapeutic. FIGS. 1A–1F, 2A–2F, 3A–3D, and 5A–5D, and Tables 1 and 2 provide additional gene products which can be useful in evaluating the efficacy of treatment.

The present invention also provides information regarding the genes that are important in MLL treatment response, thereby providing additional targets for diagnosis and therapy. It is also clear that the present invention can be used to generate databases comprising informative genes which will have many applications in medicine, research and industry.

Also encompassed in the present invention is the use of gene expression profiles to screen for therapeutic agents. In one embodiment, the present invention is directed to a method of screening for a therapeutic agent for an individual with mixed lineage leukemia, comprising isolating a gene expression product from at least one informative gene from one or more cells of the individual with mixed lineage leukemia; identifying a therapeutic agent by determining a gene expression profile of at least one informative gene before and after administration of the agent, wherein if the gene expression profile from the individual after administration of the agent is correlated with effective treatment of mixed lineage leukemia the agent is identified as a therapeutic agent. In another embodiment, the cells are selected from the group consisting of mononuclear blood cells and bone marrow cells. Alternatively, the above method can utilize a cell line derived from an individual with mixed lineage leukemia.

The invention also provides methods (also referred to herein as "screening assays") for identifying agents or compounds (e.g., fusion proteins, polypeptides, peptidomimetics, prodrugs, receptors, binding agents, antibodies, small molecules or other drugs, or ribozymes) that alter or modulate (e.g., increase or decrease) the activity of the gene expression products of the informative genes (e.g., polypeptides encoded by the informative genes) as described herein, or that otherwise interact with the informative genes and/or polypeptides described herein. Such compounds can be compounds or agents that bind to informative gene expression products described herein (e.g., the polypeptides encoded by the informative genes in FIGS. 1A–1F, 2A–2F, 3A–3D, and 5A–5D, and Tables 1 and 2), and that have a stimulatory or inhibitory effect on, for example, activity of the polypeptide encoded by an informative gene described herein; or that change (e.g., enhance or inhibit) the ability of a polypeptide encoded by an informative gene to interact with compounds or agents that bind such an informative gene polypeptide; or that alter post-translational processing of such a polypeptide (e.g., agents that alter proteolytic processing to direct the polypeptide from where it is normally synthesized to another location in the cell, such as the cell surface or the nucleus; or agents that alter proteolytic processing such that more polypeptide is released from the cell, etc.). In one example, the binding agent is an MLL binding agent. As used herein, by an MLL binding agent" is meant an agent as described herein that binds to a polypeptide encoded by an informative gene of the present invention and modulates the occurrence, severity, or progression of mixed lineage leukemia. The modulation can be an increase or a decrease in the occurrence, severity, or progression of prostate cancer. In addition, an MLL binding agent includes an agent that binds to a polypeptide that is upstream (earlier) or downstream (later) of the cell signaling events mediated by a polypeptide encoded by an informative gene of the present invention, and thereby modulates the overall activity of the signaling pathway; in turn, the mixed lineage leukemia disease state of is modulated.

The candidate compound can cause an alteration in the activity of a polypeptide encoded by an informative gene of the present invention. For example, the activity of the polypeptide can be altered (increased or decreased) by at least 1.5-fold to 2-fold, at least 3-fold, or, at least 5-fold, relative to the control. Alternatively, the polypeptide activity can be altered, for example, by at least 10%, at least 20%, 40%, 50%, or 75%, or by at least 90%, relative to the control.

In one embodiment, the invention provides assays for screening candidate compounds or test agents to identify compounds that bind to or modulate the activity of a polypeptide encoded by an informative gene described herein (or biologically active portion(s) thereof), as well as agents identifiable by the assays. As used herein, a "candidate compound" or "test agent" is a chemical molecule, be it naturally-occurring or artificially-derived, and includes, for example, peptides, proteins, synthesized molecules, for example, synthetic organic molecules, naturally-occurring molecule, for example, naturally occurring organic molecules, nucleic acid molecules, and components thereof.

In general, candidate compounds for use in the present invention may be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available, e.g., from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are generated, if desired, according to methods known in the art, e.g., by standard extraction and fractionation methods. For example, candidate compounds can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to polypeptide libraries, while the other four approaches are applicable to polypeptide, non-peptide oligomer or small molecule libraries of compounds (Lam, Anticancer Drug Des., 12: 145 (1997)). Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their activities should be employed whenever possible.

When a crude extract is found to modulate (i.e., stimulate or inhibit) the expression and/or activity of the informative genes and/or their encoded polypeptides, further fractionation of the positive lead extract is necessary to isolate chemical constituents responsible for the observed effect. Thus, the goal of the extraction, fractionation, and purification process is the careful characterization and identification of a chemical entity within the crude extract having an activity that stimulates or inhibits nucleic acid expression, polypeptide expression, or polypeptide biological activity. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using animal models for diseases in which it is desirable to alter the activity or expression of the nucleic acids or polypeptides of the present invention.

In one embodiment, to identify candidate compounds that alter the biological activity of a polypeptide encoded by an informative gene as described herein, a cell, tissue, cell lysate, tissue lysate, or solution containing or expressing a polypeptide encoded by the informative gene (e.g., a polypeptide encoded by a gene in any of FIGS. 1A–1F, 2A–2F, 3A–3D, and 5A–5D, and Tables 1 and 2), or a fragment or derivative thereof, can be contacted with a candidate compound to be tested under conditions suitable for biological activity of the polypeptide. Alternatively, the polypeptide can be contacted directly with the candidate compound to be tested. The level (amount) of polypeptide biological activity is assessed/measured, either directly or indirectly, and is compared with the level of biological activity in a control (i.e., the level of activity of the polypeptide or active fragment or derivative thereof in the absence of the candidate compound to be tested, or in the presence of the candidate compound vehicle only). If the level of the biological activity in the presence of the candidate compound differs, by an amount that is statistically significant, from the level of the biological activity in the absence of the candidate compound, or in the presence of the candidate compound vehicle only, then the candidate compound is a compound that alters the biological activity of the polypeptide encoded by an informative gene of the invention. For example, an increase in the level of polypeptide biological activity relative to a control, indicates that the candidate compound is a compound that enhances (is an agonist of) the polypeptide biological activity. Similarly, a decrease in the polypeptide biological activity relative to a control, indicates that the candidate compound is a compound that inhibits (is an antagonist of) the polypeptide biological activity.

In another embodiment, the level of biological activity of a polypeptide encoded by an informative gene, or a derivative or fragment thereof in the presence of the candidate compound to be tested, is compared with a control level that has previously been established. A level of polypeptide biological activity in the presence of the candidate compound that differs from (i.e., increases or decreases) the control level by an amount that is statistically significant indicates that the compound alters the biological activity of the polypeptide.

The present invention also relates to an assay for identifying compounds (e.g., antisense nucleic acids, fusion proteins, polypeptides, peptidomimetics, prodrugs, receptors, binding agents, antibodies, small molecules or other drugs, or ribozymes) that alter (e.g., increase or decrease) expression (e.g., transcription or translation) of an informative gene or that otherwise interact with an informative gene described herein, as well as compounds identifiable by the assays. For example, a solution containing an informative gene can be contacted with a candidate compound to be tested. The solution can comprise, for example, cells containing the informative gene or cell lysate containing the informative gene; alternatively, the solution can be another solution that comprises elements necessary for transcription/translation of the informative gene. Cells not suspended in solution can also be employed, if desired. The level and/or pattern of informative gene expression (e.g., the level and/or pattern of mRNA or protein expressed) is assessed, and is compared with the level and/or pattern of expression in a control (i.e., the level and/or pattern of the informative gene expressed in the absence of the candidate compound, or in the presence of the candidate compound vehicle only). If the expression level and/or pattern in the presence of the candidate compound differs by an amount or in a manner that is statistically significant from the level and/or pattern in the absence of the candidate compound, or in the presence of the candidate compound vehicle only, then the candidate compound is a compound that alters the expression of an informative gene. Enhancement of informative gene expression indicates that the candidate compound is an agonist of informative gene polypeptide activity. Similarly, inhibition of informative gene expression indicates that the candidate compound is an antagonist of informative gene polypeptide activity.

In another embodiment, the level and/or pattern of an informative gene in the presence of the candidate compound to be tested, is compared with a control level and/or pattern that has previously been established. A level and/or pattern informative gene expression in the presence of the candidate compound that differs from the control level and/or pattern by an amount or in a manner that is statistically significant indicates that the candidate compound alters informative gene expression.

In another embodiment of the invention, compounds that alter the expression of an informative gene, or that otherwise interact with an informative gene described herein, can be identified using a cell, cell lysate, or solution containing a nucleic acid encoding the promoter region of the informative gene operably linked to a reporter gene. As used herein by "promoter" means a minimal nucleotide sequence sufficient to direct transcription, and by "operably linked" means that a gene and one or more regulatory sequences are connected in such a way as to permit gene expression when the appropriate molecules (e.g., transcriptional activator proteins) are bound to the regulatory sequences. Examples of reporter genes and methods for operably linking a reporter gene to a promoter are known in the art. After contact with a candidate compound to be tested, the level of expression of the reporter gene (e.g., the level of mRNA or of protein expressed) is assessed, and is compared with the level of expression in a control (i.e., the level of expression of the reporter gene in the absence of the candidate compound, or in the presence of the candidate compound vehicle only). If the level of expression in the presence of the candidate compound differs by an amount or in a manner that is statistically significant from the level in the absence of the candidate compound, or in the presence of the candidate compound vehicle only, then the candidate compound is a compound that alters the expression of the informative gene, as indicated by its ability to alter expression of the reporter gene that is operably linked to the informative gene promoter. Enhancement of the expression of the reporter gene indicates that the compound is an agonist of the informative gene polypeptide activity. Similarly, inhibition of the expression of the reporter gene indicates that the compound is an antagonist of the informative gene polypeptide activity.

In another embodiment, the level of expression of the reporter in the presence of the candidate compound to be tested, is compared with a control level that has been established previously. A level in the presence of the candidate compound that differs from the control level by an amount or in a manner that is statistically significant indicates that the candidate compound alters informative gene expression.

The present invention also features methods of detecting and/or identifying a compound that alters the interaction between a polypeptide encoded by an informative gene and a polypeptide (or other molecule) with which the polypeptide normally interacts with (e.g., in a cell or under physiological conditions). In one example, a cell or tissue that expresses or contains a compound (e.g., a polypeptide or other molecule) that interacts with a polypeptide encoded by an informative gene (such a molecule is referred to herein as a "polypeptide substrate") is contacted with the informative gene polypeptide in the presence of a candidate compound, and the ability of the candidate compound to alter the interaction between the polypeptide encoded by the informative gene and the polypeptide substrate is determined, for example, by assaying activity of the polypeptide. Alternatively, a cell lysate or a solution containing the informative gene polypeptide, the polypeptide substrate, and the candidate compound can be used. A compound that binds to the informative gene polypeptide or to the polypeptide substrate can alter the interaction between the informative gene polypeptide and the polypeptide substrate by interfering with (inhibiting), or enhancing the ability of the informative gene polypeptide to bind to, associate with, or otherwise interact with the polypeptide substrate.

Determining the ability of the candidate compound to bind to the informative gene polypeptide or a polypeptide substrate can be accomplished, for example, by coupling the candidate compound with a radioisotope or enzymatic label such that binding of the candidate compound to the informative gene polypeptide or polypeptide substrate can be determined by directly or indirectly detecting the candidate compound labeled with $^{125}I$, $^{35}S$, $^{14}C$, or $^{3}H$, and the detecting the radioisotope (e.g., by direct counting of radioemmission or by scintillation counting). Alternatively, the candidate compound can be enzymatically labeled with, for example, horseradish peroxidase, alkaline phosphatase, or luciferase, and the enzymatic label is then detected by determination of conversion of an appropriate substrate to product. In another alternative, one of the other components of the screening assay (e.g., the polypeptide substrate or the informative gene polypeptide) can be labeled, and alterations in the interaction between the informative gene polypeptide and the polypeptide substrate can be detected. In these methods, labeled unbound components can be removed (e.g., by washing) after the interaction step in order to accurately detect the effect of the candidate compound on the interaction between the informative gene polypeptide and the polypeptide substrate.

It is also within the scope of this invention to determine the ability of a candidate compound to interact with the informative gene polypeptide or polypeptide substrate without the labeling of any of the interactants. For example, a microphysiometer can be used to detect the interaction of a candidate compound with a polypeptide encoded by an informative gene or a polypeptide substrate without the labeling of either the candidate compound, the polypeptide encoded by the informative gene, or the polypeptide substrate (McConnell et al., Science 257: 1906–1912 (1992)). As used herein, a "microphysiometer" (e.g., CYTOSENSOR™) is an analytical instrument that measures the rate at which a cell acidifies its environment using a light-addressable potentiometric sensor (LAPS). Changes in this acidification rate can be used as an indicator of the interaction between ligand and polypeptide.

In another embodiment of the invention, assays can be used to identify polypeptides that interact with one or more polypeptides encoded by an informative gene. For example, a yeast two-hybrid system such as that described by Fields and Song (Fields and Song, Nature 340: 245–246 (1989)) can be used to identify polypeptides that interact with one or more polypeptides encoded by an informative gene. In such a yeast two-hybrid system, vectors are constructed based on the flexibility of a transcription factor that has two functional domains (a DNA binding domain and a transcription activation domain). If the two domains are separated but fused to two different proteins that interact with one another, transcriptional activation can be achieved, and transcription of specific markers (e.g., nutritional markers such as His and Ade, or color markers such as lacZ) can be used to identify the presence of interaction and transcriptional activation. For example, in the methods of the invention, a first vector is used that includes a nucleic acid encoding a DNA binding domain and a polypeptide encoded by an informative gene, or fragment or derivative thereof, and a second vector is used that includes a nucleic acid encoding a transcription activation domain and a nucleic acid encoding a polypeptide that potentially may interact with the informative gene polypeptide, or fragment or derivative thereof. Incubation of yeast containing the first vector and the second vector under appropriate conditions (e.g., mating conditions such as used in the MATCHMAKER™ system from Clontech) allows identification of colonies that express the markers of the polypeptide(s). These colonies can be examined to identify the polypeptide(s) that interact with the polypeptide encoded by the informative gene or a fragment or derivative thereof. Such polypeptides may be useful as compounds that alter the activity or expression of an informative gene polypeptide.

In more than one embodiment of the above assay methods of the present invention, it may be desirable to immobilize a polypeptide encoded by an informative gene, or a polypeptide substrate, or other components of the assay on a solid support, in order to facilitate separation of complexed from uncomplexed forms of one or both of the polypeptides, as well as to accommodate automation of the assay. Binding of a candidate compound to the polypeptide, or interaction of the polypeptide with a polypeptide substrate in the presence and absence of a candidate compound, can be accomplished in any vessel suitable for containing the reactants. Examples of such vessels include microtitre plates, test tubes, and micro-centrifuge tubes. In one embodiment, a fusion protein (e.g., a glutathione-S-transferase fusion protein) can be provided that adds a domain that allows the informative gene polypeptide, or the polypeptide substrate to be bound to a matrix or other solid support.

This invention further pertains to novel compounds identified by the above-described screening assays. Accordingly, it is within the scope of this invention to further use a compound identified as described herein in an appropriate animal model. For example, a compound identified as described herein can be used in an animal model to determine the efficacy, toxicity, or side effects of treatment with such a compound. Alternatively, a compound identified as described herein can be used in an animal model to determine the mechanism of action of such a compound. Furthermore, this invention pertains to uses of novel compounds identified by the above-described screening assays for treatments as described herein. In addition, a compound identified as described herein can be used to alter activity of a polypeptide encoded by an informative gene, or to alter expression of the informative gene, by contacting the polypeptide or the nucleic acid molecule (or contacting a cell comprising the polypeptide or the nucleic acid molecule) with the compound identified as described herein.

The present invention encompasses a method of treating MLL, AML or ALL, comprising the administration of an agent which modulates the expression level or activity of an informative gene product. A therapeutic agent may increase or decrease the level or activity of the gene product. For example, an inhibitor of the kinase FLT3 could be useful in treating MLL. Other suitable therapeutic targets for drug development include genes described herein in FIGS. 1A–1F, 2A–2F, 3A–3D, and 5A–5D, and Tables 1 and 2.

The present invention further relates to antibodies that specifically bind a polypeptide, preferably an epitope, of an informative gene of the present invention (as determined, for example, by immunoassays, a technique well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, for example, anti-Id antibodies to antibodies of the invention), and epitope-binding fragments of any of the above.

The term "antibody," as used herein, refers to immunoglobulin molecules and immunologically active portions of immunoglobulin molecules, and more specifically, molecules that contain an antigen binding site that specifically binds an antigen. The immunoglobulin molecules of the invention can be of any type (for example, IgG, IgE, IgM, IgD, IgA and IgY), and of any class (for example, IgG1, IgG2, IgG3, IgG4, IgA1 and IgA2) or subclass of an immunoglobulin molecule.

In one embodiment, the antibodies are antigen-binding antibody fragments and include, without limitation, Fab, Fab' and F(ab')$_2$, Fd, single-chain Fvs (scFv), single-chain antibodies, disulfide-linked Fvs (sdFv) and fragments comprising either a $V_L$ or $V_H$ domain. Antigen-binding antibody fragments, including single-chain antibodies, can comprise the variable region(s) alone or in combination with the entirety or a portion of one or more of the following: hinge region, CH1, CH2, and CH3 domains. Also included in the invention are antigen-binding fragments also comprising any combination of variable region(s) with a hinge region, CH1, CH2, and/or CH3 domains.

The antibodies of the invention may be from any animal origin including birds and mammals. Preferably, the antibodies are human, murine, donkey, sheep, rabbit, goat, guinea pig, hamster, horse, or chicken.

As used herein, "human" antibodies include antibodies having the amino acid sequence of a human immunoglobulin and include antibodies produced by human B cells, or isolated from human sera, human immunoglobulin libraries or from animals transgenic for one or more human immunoglobulins and that do not express endogenous immunoglobulins, as described in U.S. Pat. No. 5,939,598 by Kucherlapati et al., for example.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material.

Antibodies of the present invention may be described or specified in terms of the epitope(s) or portion(s) of a polypeptide of the present invention that they recognize or specifically bind. The epitope(s) or polypeptide portion(s) may be specified, for example, by N-terminal and/or C-terminal positions, or by size in contiguous amino acid residues. Antibodies that specifically bind any epitope or polypeptide encoded by an informative gene of the present invention may also be excluded. Therefore, the present invention includes antibodies that specifically bind a polypeptide encoded by an informative gene of the present invention, and allows for the exclusion of the same.

The term "epitope," as used herein, refers to a portion of a polypeptide which contacts an antigen-binding site(s) of an antibody or T cell receptor. Specific binding of an antibody to an antigen having one or more epitopes excludes non-specific binding to unrelated antigens, but does not necessarily exclude cross-reactivity with other antigens with similar epitopes.

Antibodies of the present invention may also be described or specified in terms of their cross-reactivity. Antibodies of the present invention may not display any cross-reactivity, such that they do not bind any other analog, ortholog, or homolog of a polypeptide of the present invention. Alternatively, antibodies of the invention can bind polypeptides with at least about 95%, 90%, 85%, 80%, 75%, 70%, 65%, 60%, 55%, or 50% identity (as calculated using methods known in the art) to a polypeptide encoded by an informative gene of the present invention. Further included in the present invention are antibodies that bind polypeptides encoded by informative genes that hybridize to an informative gene of the present invention under stringent hybridization conditions, as will be appreciated by one of skill in the art.

Antibodies of the present invention can also be described or specified in terms of their binding affinity to a polypeptide of the invention. Preferred binding affinities include those with a dissociation constant or Kd less than $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$M, $5\times10^{-11}$M $10^{-11}$ M, $5\times10^{-12}$ M, $10^{-12}$ M, $5\times10^{-13}$ M, $10^{-13}$ M, $5\times10^{-14}$ M, $10^{-13}$ M, $5\times10^{-15}$ M, and $10^{-15}$ M.

The invention also provides antibodies that competitively inhibit binding of an antibody to an epitope of a polypeptide of the invention, as determined by any method known in the art for determining competitive binding, for example, using immunoassays. In particular embodiments, the antibody competitively inhibits binding to the epitope by at least about 90%, 80%, 70%, 60%, or 50%.

Antibodies of the present invention can act as agonists or antagonists of polypeptides encoded by the informative genes of the present invention. For example, the present invention includes antibodies which disrupt interactions with the polypeptides encoded by the informative genes of the invention either partially or fully. The invention also includes antibodies that do not prevent binding, but prevent activation or activity of the polypeptide. Activation or activity (for example, signaling) may be determined by techniques known in the art. Also included are antibodies that prevent both binding to and activity of a polypeptide encoded by an informative gene. Likewise included are neutralizing antibodies.

Antibodies of the present invention may be used, for example, and without limitation, to purify, detect, and target the polypeptides encoded by the informative genes described herein, including both in vitro and in vivo diagnostic and therapeutic methods. For example, the antibodies have use in immunoassays for qualitatively and quantitatively measuring levels of the polypeptides in biological samples. See, for example, Harlow et al., Antibodies: A Laboratory Manual (Cold Spring Harbor Laboratory Press, 2nd ed. 1988).

As discussed in more detail below, the antibodies of the present invention may be used either alone or in combination with other compositions. The antibodies may further be recombinantly fused to a heterologous polypeptide at the N- and/or C-terminus or chemically conjugated (including covalent and non-covalent conjugations) to polypeptides or other compositions. For example, antibodies of the present invention may be recombinantly fused or conjugated to molecules useful as labels in detection assays, or effector molecules such as heterologous polypeptides, drugs, or toxins.

The antibodies of the invention include derivatives that are modified, for example, by the covalent attachment of any type of molecule to the antibody such that covalent attachment does not prevent the antibody from recognizing its epitope. For example, but not by way of limitation, the antibody derivatives include antibodies that have been modified, for example, by glycosylation, acetylation, pegylation, phosphorylation, amidation, derivatization by known protecting/blocking groups, proteolytic cleavage, or linkage to a cellular ligand or other protein. Any of numerous chemical modifications can be carried out by known techniques, including, but not limited to, specific chemical cleavage, acetylation, formylation, and metabolic synthesis of tunicamycin. Additionally, the derivative can contain one or more non-classical amino acids.

The antibodies of the present invention can be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, or the like, to induce the production of sera containing polyclonal antibodies specific for the antigen. Various adjuvants can be used to increase the immunological response, depending on the host species, and include, but are not limited to, Freund's adjuvant (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and corynebacterium parvum. Such adjuvants are well known in the art.

Monoclonal antibodies can be prepared using a wide variety of techniques also known in the art, including hybridoma cell culture, recombinant, and phage display technologies, or a combination thereof. For example, monoclonal antibodies can be produced using hybridoma techniques as is known in the art and taught, for example, in Harlow et al., Antibodies: A Laboratory Manual (Cold Spring Harbor Laboratory Press, 2nd ed. 1988). The term "monoclonal antibody" as used herein is not necessarily limited to antibodies produced through hybridoma technology, but also refers to an antibody that is derived from a single clone, including any eukaryotic, prokaryotic, or phage clone.

Human antibodies are desirable for therapeutic treatment of human patients. These antibodies can be made by a variety of methods known in the art including phage display methods using antibody libraries derived from human immunoglobulin sequences. Human antibodies can also be produced using transgenic mice that are incapable of expressing functional endogenous immunoglobulins, but which can express human immunoglobulin genes. The transgenic mice are immunized with a selected antigen, for example, all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For a detailed discussion of this technology for producing human antibodies and human monoclonal antibodies and protocols for producing such antibodies, see, for example, PCT publications WO 98/24893; WO 96/34096; WO 96/33735; and U.S. Pat. Nos. 5,413,923; 5,625,126; 5,633,425; 5,569,825; 5,661,016; 5,545,806; 5,814,318; and 5,939,598.

In another embodiment, antibodies to the polypeptides encoded by the informative genes as described herein can, in turn, be utilized to generate anti-idiotype antibodies that "mimic" polypeptides of the invention using techniques well known to those skilled in the art. (See, for example, Greenspan & Bona, FASEB J. 7(5):437–444 (1989) and Nissinoff, J. Immunol. 147(8):2429–2438 (1991)). For example, antibodies that bind to and competitively inhibit polypeptide multimerization and/or binding of a polypeptide to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide encoded by an informative gene and/or to bind its ligands, and thereby block its biological activity.

The antibodies or fragments thereof of the present invention can be fused to marker sequences, such as a peptide to facilitate their purification. In one embodiment, the marker amino acid sequence is a hexa-histidine peptide, an HA tag, or a FLAG tag, as will be readily appreciated by one of skill in the art.

The present invention further encompasses antibodies or fragments thereof conjugated to a diagnostic or therapeutic agent. The antibodies can be used diagnostically, for example, to monitor the development or progression of a tumor as part of a clinical testing procedure to determine the efficacy of a given treatment regimen. Detection can be facilitated by coupling the antibody to a detectable substance. Examples of detectable substances include enzymes (such as, horseradish peroxidase, alkaline phosphatase, beta-galactosidase, or acetylcholinesterase), prosthetic group (such as streptavidin/biotin and avidin/biotin), fluorescent materials (such as umbelliferone, fluorescein, fluorescein isothiocyanate, rhodamine, dichlorotriazinylamine fluorescein, dansyl chloride or phycoerythrin), luminescent materials (such as luminol), bioluminescent materials (such as luciferase, luciferin, and aequorin), radioactive materials (such as, $^{125}$I, $^{131}$I, $^{111}$In or $^{99}$Tc), and positron emitting metals using various positron emission tomographies, and nonradioactive paramagnetic metal ions.

In an additional embodiment, an antibody or fragment thereof can be conjugated to a therapeutic moiety such as a cytotoxin, for example, a cytostatic or cytocidal agent, a therapeutic agent or a radioactive metal ion. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (for example, daunorubicin (formerly daunomycin) and doxorubicin), antibiotics (for example, actinomycin, bleomycin, mithramycin, and anthramycin (AMC)), and anti-mitotic agents (for example, vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, a thrombotic agent or an anti-angiogenic agent, for example, angiostatin or endostatin; or, biological response modifiers such as, for example, lymphokines, interleukins, granulocyte macrophase colony stimulating factor ("GM-CSF"), granulocyte colony stimulating factor ("G-CSF"), or other growth factors.

Antibodies of the invention can also be attached to solid supports. These are particularly useful for immunoassays or purification of the target antigen. Such solid supports include, but are not limited to, glass, cellulose, silicon, polyacrylamide, nylon, polystyrene, polyvinyl chloride or polypropylene. Techniques for conjugating such therapeutic moiety to antibodies are well known in the art, see, for example, Arnon et al., "Monoclonal Antibodies For Immunotargeting Of Drugs In Cancer Therapy", in Monoclonal Antibodies And Cancer Therapy, Reisfeld et al. eds., pp. 243–56 (Alan R. Liss, Inc. 1985).

Alternatively, an antibody can be conjugated to a second antibody to form an antibody heteroconjugate as described by Segal in U.S. Pat. No. 4,676,980.

An antibody of the invention, with or without conjugation to a therapeutic moiety, administered alone or in combination with cytotoxic factor(s) and/or cytokine(s), can be used as a therapeutic.

Antisense antagonists of the present invention are also included. Antisense technology can be used to control gene expression through antisense DNA or RNA, or through triple-helix formation. Antisense techniques are discussed for example, in Okano, J., Neurochem. 56:560 (1991). The methods are based on binding of a polynucleotide to a complementary DNA or RNA. In one embodiment, an antisense sequence is generated internally by the organism, in another embodiment, the antisense sequence is separately administered (see, for example, O'Connor, J., Neurochem. 56:560 (1991)).

In one embodiment, the 5' coding portion of an informative gene can be used to design an antisense RNA oligonucleotide from about 10 to 40 base pairs in length. Generally, a DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid of the invention. Such a vector contains the sequence encoding the antisense nucleic acid. The vector can remain episomal or become chromosomally integrated, as long as it can be transcribed to produce the desired antisense RNA. Vectors can be constructed by recombinant DNA technology and can be plasmid, viral, or otherwise, as is known to one of skill in the art.

Expression can be controlled by any promoter known in the art to act in the target cells, such as vertebrate cells, and preferably human cells. Such promoters can be inducible or constitutive and include, without limitation, the SV40 early promoter region (Bemoist and Chambon, Nature 29:304–310(1981), the promoter contained in the 3' long terminal repeat of Rous sarcoma virus (Yamamoto et al., Cell 22:787–797 (1980)), the herpes thymidine promoter (Wagner et al., Proc. Natl. Acad. Sci. U.S.A. 78:1441–1445 (1981)), and the regulatory sequences of the metallothionein gene (Brinster et al., Nature 296:39–42 (1982)).

The antisense nucleic acids of the invention comprise a sequence complementary to at least a portion of an RNA transcript of an informative gene. Absolute complementarity, although preferred, is not required. A sequence "complementary to at least a portion of an RNA," referred to herein, means a sequence having sufficient complementarity to be able to hybridize with the RNA, forming a stable duplex. The ability to hybridize will depend on both the degree of complementarity and the length of the antisense nucleic acid. Generally, the larger the hybridizing nucleic acid, the more base mismatches with the RNA it may contain and still form a stable duplex. One skilled in the art can ascertain a tolerable degree of mismatch by use of standard procedures to determine the melting point of the hybridized complex.

Oligonucleotides that are complementary to the 5' end of the RNA, for example, the 5' untranslated sequence up to and including the AUG initiation codon, are generally regarded to work most efficiently at inhibiting translation. However, sequences complementary to the 3' untranslated sequences of mRNAs have been shown to be effective at inhibiting translation of mRNAs as well. Thus, oligonucleotides complementary to either the 5'- or 3'-non-translated, non-coding regions of a nucleotide sequence can be used in an antisense approach to inhibit mRNA translation. Oligonucleotides complementary to the 5' untranslated region of the mRNA can include the complement of the AUG start codon. Antisense oligonucleotides complementary to mRNA coding regions can also be used in accordance with the invention. In one embodiment, the antisense nucleic acids are at least six nucleotides in length, and are preferably oligonucleotides ranging from about 6 to about 50 nucleotides in length. In other embodiments, the oligonucleotide is at least about 10, 17, 25 or 50 nucleotides in length.

The antisense oligonucleotides of the invention can be DNA or RNA, or chimeric mixtures, or derivatives or modified versions thereof, single-stranded or double-stranded. The oligonucleotide can be modified at the base moiety, sugar moiety, or phosphate backbone, for example, to improve stability of the molecule, hybridization, and the like. The oligonucleotide can include other appended groups such as peptides (for example, to target host cell receptors in vivo), or agents that facilitate transport across the cell membrane, or the blood-brain barrier, or intercalating agents.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, a-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., Nucl. Acids Res. 15:6625–6641 (1987)). The oligonucleotide is a 2'-O-methylribonucleotide (Inoue et al., Nucl. Acids Res. 15:6131–6148 (1987)), or a chimeric RNA-DNA analog (Inoue et al., FEBS Lett. 215:327–330 (1987)).

Antisense oligonucleotides of the invention may be synthesized by standard methods known in the art, for example, by use of an automated DNA synthesizer.

Potential antagonists according to the invention also include catalytic RNA, or a ribozyme. Hammerhead ribozymes cleave mRNAs at locations dictated by flanking regions that form complementary base pairs with the target mRNA. The target mRNA has the following sequence of two bases: 5'-UG-3'. The construction and production of hammerhead ribozymes is well known in the art and is described more fully in Haseloff and Gerlach (Nature 334:585–591 (1988)). Preferably, the ribozyme is engineered so that the cleavage recognition site is located near the 5' end of the mRNA in order to increase efficiency and minimize the intracellular accumulation of non-functional mRNA transcripts.

Ribozymes of the invention can be composed of modified oligonucleotides (for example for improved stability, targeting, and the like). DNA constructs encoding the ribozyme can be under the control of a strong constitutive promoter, such as, for example, pol III or pol II promoter, so that a transfected cell will produce sufficient quantities of the ribozyme to destroy endogenous target mRNA and inhibit translation. Since ribozymes, unlike antisense molecules, are catalytic, a lower intracellular concentration is generally required for efficiency.

The present invention also provides pharmaceutical compositions, including both therapeutic and prophylatic compositions. Compositions within the scope of this invention include all compositions wherein the therapeutic abent, antibody, fragment or derivative, antisense oligonucleotide or ribozyme is contained in an amount effective to achieve its intended purpose. While individual needs vary, determination of optimal ranges of effective amounts of each component is within the skill of the art. The effective dose is a function of a number of factors, including the specific antibody, the antisense construct, ribozyme or polypeptide of the invention, the presence of a conjugated therapeutic agent (see below), the patient and their clinical status.

Mode of administration may be by parenteral, subcutaneous, intravenous, intramuscular, intraperitoneal, transdermal, or buccal routes. Alternatively, or concurrently, administration may be orally. The dosage administered will be dependent upon the age, health, and weight of the recipient, kind of concurrent treatment, if any, frequency of treatment, and the nature of the effect desired.

Such compositions generally comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skimmed milk, glycerol, propylene, glycol, water, ethanol and the like. The composition, if desired, can also contain minor amounts of wetting or emulsifying agents, or pH buffering agents.

These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, and the like. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to a human. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, and the like, and those formed with cations such as those derived from sodium, potassium, ammonium, calcium, ferric hydroxides, isopropylamine, triethylamine, 2-ethylamino ethanol, histidine, procaine, and the like.

The compositions of the invention can be administered alone or in combination with other therapeutic agents. Therapeutic agents that can be administered in combination with the compositions of the invention, include but are not limited to chemotherapeutic agents, antibiotics, steroidal and non-steroidal anti-inflammatories, conventional immunotherapeutic agents, cytokines and/or growth factors. Combinations may be administered either concomitantly, for example, as an admixture, separately but simultaneously or concurrently; or sequentially. This includes presentations in which the combined agents are administered together as a therapeutic mixture, and also procedures in which the combined agents are administered separately but simultaneously, for example, as through separate intravenous lines into the same individual. Administration "in combination" further includes the separate administration of one of the compounds or agents given first, followed by the second.

Conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergulin, and other immunosuppressive agents.

In a further embodiment, the compositions of the invention are administered in combination with an antibiotic agent. Antibiotic agents that may be administered with the compositions of the invention include, but are not limited to, tetracycline, metronidazole, amoxicillin, beta-lactamases, aminoglycosides, macrolides, quinolones, fluoroquinolones, cephalosporins, erythromycin, ciprofloxacin, and streptomycin.

In an additional embodiment, the compositions of the invention are administered alone or in combination with an anti-inflammatory agent. Anti-inflammatory agents that can be administered with the compositions of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the invention are administered in combination with cytokines. Cytokines that may be administered with the compositions of the invention include, but are not limited to, IL2, IL3, IL4, IL5, IL6, IL7, IL10, IL12, IL13, IL15, anti-CD40, CD40L, IFN-gamma and TNF-alpha.

In additional embodiments, the compositions of the invention are administered in combination with other therapeutic or prophylactic regimens, such as, for example, radiation therapy.

The present invention is further directed to therapies which involve administering pharmaceutical compositions of the invention to an animal, preferably a mammal, and most preferably a human patient for treating one or more of the described disorders. Therapeutic compositions of the invention include, for example, therapeutic agents identified in screening assays, antibodies of the invention (including fragments, analogs and derivatives thereof as described herein), antisense oligonucleotides, ribozymes and nucleic acids encoding same. The compositions of the invention can be used to treat, inhibit, prognose, diagnose or prevent diseases, disorders or conditions associated with aberrant expression and/or activity of a polypeptide of the invention, including, but not limited to, any one or more of the diseases, disorders, or conditions such as, for example, MLL, AML, or ALL.

The treatment and/or prevention of diseases and disorders associated with aberrant expression and/or activity of a polypeptide of the invention includes, but is not limited to, alleviating symptoms associated with those diseases and disorders.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Furthermore, the dosage and frequency of administration of antibodies of the invention may be reduced by enhancing uptake and tissue penetration of the antibodies by modifications such as, for example, lipidation or addition of cell-specific tags.

The compounds or pharmaceutical compositions of the invention can be tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

The invention provides methods of treatment, inhibition and prophylaxis by administration to a subject of an effective amount of a compound or pharmaceutical composition of the invention. In one aspect, the compound is substantially purified such that the compound is substantially free from substances that limit its effect or produce undesired side-effects. The subject is preferably an animal, including but not limited to animals such as cows, pigs, horses, chickens, cats, dogs, etc., and is preferably a mammal, and most preferably human.

Various delivery systems are known and can be used to administer a composition of the invention, for example, encapsulation in liposomes, microparticles, microcapsules, recombinant cells capable of expressing the compound, receptor-mediated endocytosis (see, e.g., Wu and Wu, J. Biol. Chem. 262:4429–4432 (1987)), construction of a nucleic acid as part of a retroviral or other vector, and the like as will be known by one of skill in the art.

Methods of introduction include, but are not limited to, intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, for example, by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, for example, in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, such as a liposome (Langer, Science 249:1527–1533 (1990)).

In yet another embodiment, the compound or composition can be delivered in a controlled release system. Furthermore, a controlled release system can be placed in proximity of the therapeutic target, thus requiring only a fraction of the systemic dose (see, e.g., Goodson, in Medical Applications of Controlled Release, supra, vol. 2, pp. 115–138 (1984)). In a further embodiment, a pump may be used. In another embodiment, polymeric materials can be used.

In a particular embodiment where the compound of the invention is a nucleic acid encoding a protein, the nucleic acid can be administered in vivo to promote expression of its mRNA and encoded protein, by constructing it as part of an appropriate nucleic acid expression vector and administering, for example, by use of a retroviral vector, or by direct injection, or by use of microparticle bombardment for example, a gene gun, or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)). Alternatively, a nucleic acid can be introduced intracellularly and incorporated within host cell DNA for expression, by homologous recombination.

The present invention also provides kits that can be used in the above methods. In one embodiment, a kit comprises a pharmaceutical composition of the invention in one or more containers.

In another embodiment, the kit is a diagnostic kit for use in testing biological samples. The kit can include a control antibody that does not react with the polypeptide of interest in addition to a specific antibody or antigen-binding fragment thereof which binds to the polypeptide (antigen) of the invention being tested for in the biological sample. Such a kit may include a substantially isolated polypeptide antigen comprising an epitope that is specifically immunoreactive with at least one anti-polypeptide antigen antibody. Further, such a kit can include a means for detecting the binding of said antibody to the antigen (for example, the antibody may be conjugated to a fluorescent compound such as fluorescein or rhodamine which can be detected by flow cytometry). In a further embodiment, the kit may include a recombinantly produced or chemically synthesized polypeptide antigen. The polypeptide antigen of the kit may also be attached to a solid support.

In an alternative embodiment, the detecting means of the above-described kit includes a solid support to which the polypeptide antigen is attached. The kit can also include a non-attached reporter-labeled anti-human antibody. Binding of the antibody to the polypeptide antigen can be detected by binding of the reporter-labeled antibody.

In an additional embodiment, the invention includes a diagnostic kit for use in screening serum samples containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In another embodiment, the antibody may be a monoclonal antibody. The detecting means of the kit can include a second, labeled monoclonal antibody. Alternatively, or in addition, the detecting means can include a labeled, competing antigen.

In one diagnostic configuration, the test serum sample is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. Generally, the reagent is washed again to remove unbound labeled antibody, and the amount of reporter associated with the reagent is determined. The reporter can be an enzyme, for example, which is detected by incubating the solid phase in the presence of a suitable fluorometric, luminescent or calorimetric substrate, as is standard in the art.

The solid surface reagent in the above assay is prepared by known techniques for attaching protein material to solid support material. Suitable solid support materials include, for example and without limitation, polymeric beads, dip sticks, 96-well plate or filter material.

The invention will be further described with reference to the following non-limiting examples. The teaching of all patents, patent applications and all other publications and websites cited herein are incorporated by reference in their entirety.

Exemplification

Invariably, MLL translocations result in the production of a chimeric protein where the $NH_2$-terminal portion of MLL is fused to the COOH-terminal portion of one of >20 fusion partners (Dimartino and Cleary, *Br J Haematol* 106:614–626 (1999)). This has prompted models of leukemogenesis in which the MLL-fusion protein may confer a gain-of-function or neomorphic properties, or alternatively represent a dominant negative that interferes with normal MLL function. Moreover, mice heterozygous for MLL (+/−) demonstrate developmental aberrations (Yu et al., Nature 378:505–508 (1995); Hess et al., Blood 90:1799–1806 (1997)), suggesting the disruption of one allele by chromosomal translocation might also manifest as haplo-insufficiency in leukemic cells.

MLL is a homeotic regulator which shares homology with Drosophila trithorax (trx) and positively regulates the maintenance of homeotic (Hox) gene expression during development (Yu et al., Nature 378:505–508 (1995)). MLL deficient mice indicate that MLL is required for proper segment identity in the axioskeletal system, and also regulates hematopoiesis (Hess et al., Blood 90:1799–1806 (1997)). As MLL normally regulates Hox gene expression, its role in leukemogenesis may include altered patterns of HOX gene expression. An expanding body of literature shows that HOX genes are important for appropriate hematopoietic development (Buske and Humphries, *Int J I Hematol* 71:301–308 (2000)). Also, the t(7;11) (p15;p15) translocation found in human acute myelogenous leukemia (AML) results in a fusion of HOXA9 to the nucleoporin NUP98 (Nakamura et al., Nat Genet 12:154–158 (1996) and Borrow et al., Nat Genet 12:159–167 (1996)). Thus, HOX genes represent one set of transcriptional targets that warrants assessment in leukemias with MLL translocation.

We hypothesized that MLL translocations maintain a gene expression program that results in a distinct form of leukemia. It was reasoned that RNA profiles might help resolve whether leukemias bearing an MLL translocation represent a truly biphenotypic leukemia of mixed identity, a conventional B-cell precursor ALL with expression of limited myeloid genes, or a less committed hematopoietic progenitor cell. Moreover, comparing gene expression profiles of lymphoblastic leukemias with and without rearranged MLL is important because of their dramatically different response to standard ALL therapy, and because such analysis may identify new molecular targets for therapeutic approaches. The expression profiles reported here reveal that lymphoblastic leukemias bearing MLL translocations display a remarkably uniform and highly distinct pattern that clearly distinguishes them from conventional ALL or AML and warrants designation as a distinct disease, MLL.

Methods

Patient samples. After informed consent was obtained, leukemia samples were obtained from peripheral blood or bone marrow from patients at diagnosis or relapse. When the samples were obtained from peripheral blood, the percentage of blasts was greater than 60% of the total white blood cells present. Fifteen of the samples with an MLL translocation and all of the conventional childhood ALL samples were obtained from patients treated on Dana Farber Cancer Institute protocols between 1980 and 2001. Three of the infant leukemia samples with MLL rearrangements were obtained from patients treated on the Interfant99 protocol, and the two adult patients with MLL rearrangements were obtained from patients treated at Princess Margaret Hospital in Toronto. Except for one of the conventional ALL samples and four of the MLL samples that were obtained at relapse, all samples were diagnostic specimens. The AML samples have been previously described (Golub et al., Science 286:531–537 (1999)), and were from both adults and children. Eight of the MLL rearranged samples contain t(4;11), one t(9; 11), three t(11;19), one t(3;11) and one t(1;11). Six of the MLL rearrangements were detected by either FISH or Southern blot, and thus the translocation partner is unknown. The mononuclear cells were purified from red blood cells and neutrophils by ficoll-hypaque density centrifugation and either frozen in liquid nitrogen with 10% DMSO in fetal calf serum or put directly into Trizol (Life Sciences) for RNA purification.

Assessment for the presence of MLL translocations. All patient samples were assessed by standard cytogenetics. All childhood ALL patient samples were screened for the presence of a TEL-AML1 translocation by RT-PCR as previously described, Loh, M. L. et al., Blood 92:4792–4797 (1998). Any patient sample where cytogenetics failed and had no TEL-AML1 translocation was further assessed by fluoresence in situ hybridization (FISH) using a probe that spans the 11q23 breakpoint or by Southern blot (Silverman et al., Cancer 80:2285–2295 (1997); and Cuthbert et al., Genes Chromosomes Cancer 29:180–185 (2000)). AML samples were not assessed for chromosomal translocations. RNA purification, labeling and hybridization. A total of $10–20 \times 10^6$ cells were used to prepare total RNA using the Trizol (Life Sciences) purification method. This generally yielded between 5 and 20 μg of total RNA the quality of which was analyzed by gel electrophoresis. If the rRNA bands were intact, the RNA was determined to be of good quality and 5–15 μg was used for subsequent production of biotinylated cRNA as described previously (Golub et al., Science 286:531–537 (1999)), and were from both adults and children. Briefly, first strand cDNA synthesis was generated using a T7-linked oligo-dT primer, followed by second strand synthesis. An in vitro transcription reaction was done to generate the cRNA containing biotinylated UTP and CTP, which was subsequently chemically fragmented at 95° C. for 35 minutes. Samples were excluded if less than 15 μg of labeled RNA was produced. Labeled RNA was then hybridized to Affymetrix (Santa Clara, Calif.) U95A or U95A V2 oligonucleotide arrays at 45° C. for 16 hours. Arrays were washed and stained with streptavidin-phycoerytherin (SAPE, Molecular Probes). The signal was amplified using a biotinylated anti-streptavidin antibody (Vector Laboratories, Burlingame, Calif.) at 3 μg/ml. This was followed by a second staining with SAPE. Normal goat IgG was used as a blocking agent. The scans were performed on Affymetrix scanners and the expression values calculated using Affymetrix GENECHIP software. The chip image was then scanned visually for obvious differences between arrays. If there were obvious abnormalities present in the image, the sample was re-hybridized. The scans were then normalized based on a linear scaling method as described in the supplementary material. The raw expression data as obtained from Affymetrix's GeneChip s re-scaled to account for different chip intensities. Briefly, each column (sample) in the dataset was multiplied by 1/slope of a least squares linear fit of the sample versus the reference (the first sample in the dataset). This linear fit is done using only genes that have 'Present' calls in both the sample being re-scaled and the reference. The sample chosen as reference was a typical one (i.e., one with the number of "P" calls closer to the average over all samples in the dataset). Samples were disregarded if the scaling factor was greater than 3 fold.

A threshold of 100 units was imposed before analysis because at those low values the data is noisy and not very reproducible. A ceiling of 16,000 units was also imposed due to saturation effects. After this preprocessing gene expression values were subjected to a variation filter which excluded genes showing minimal variation across the samples being analyzed. The variation filter tests for a fold-change and absolute variation over samples (comparing max/min and max-min with predefined values and excluding genes not obeying both conditions). The max/min filter was 5 and the max-min 500 for all experiments.

Data analysis. Identification of genes that are correlated with particular class distinctions was performed as previously described (Golub et al., Science 286:531–537 (1999)). The signal-to-noise statistic $(\mu_0 - \mu_1)/(\sigma_0 + \sigma_0)$ was used where μ and σ represent the median and standard deviation of expression, respectively for each class. One hundred permutations of the samples were performed to determine if the correlations were greater than would be expected by chance with a 99% confidence.

Figure 6:
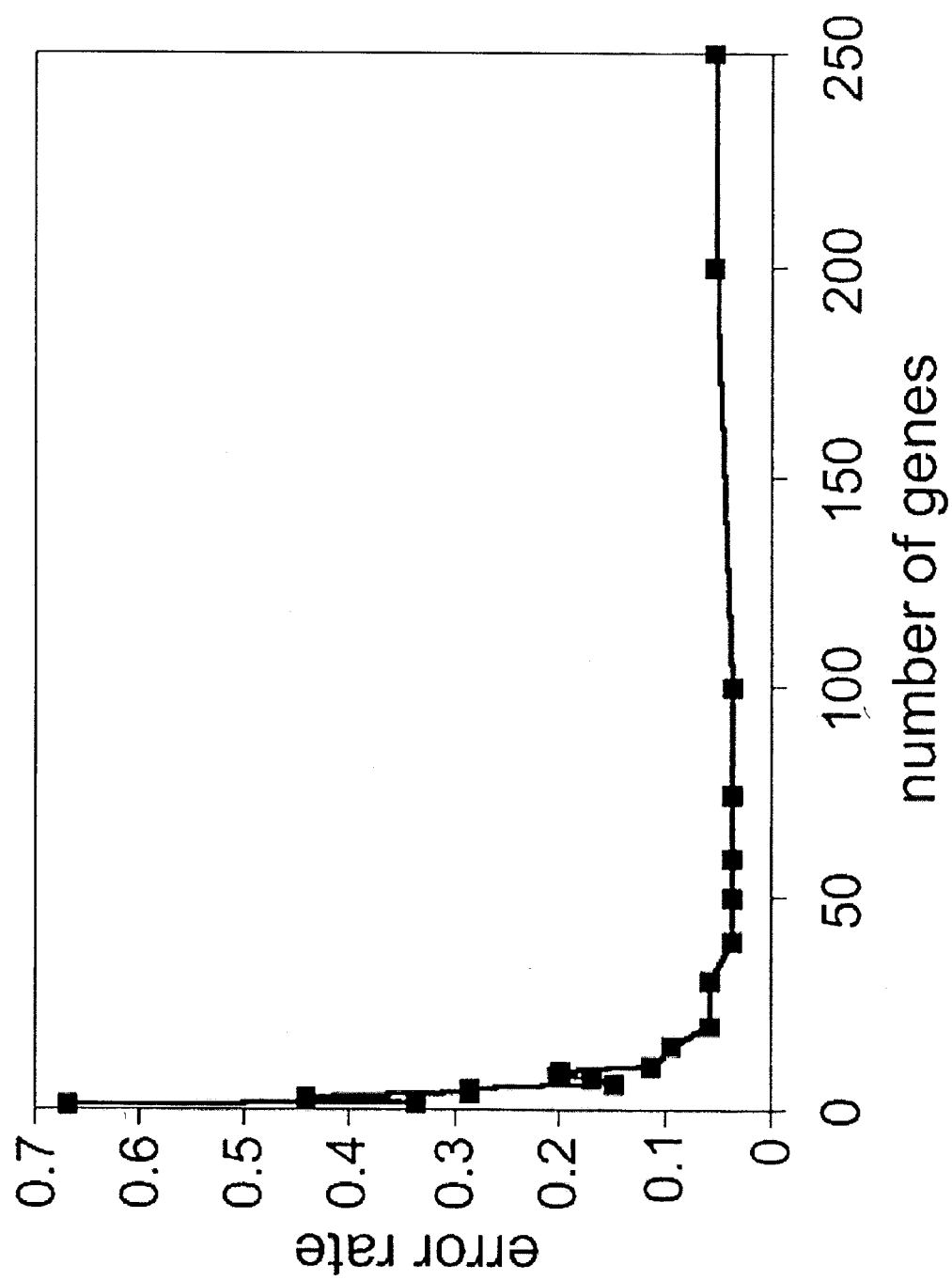
FIG. 6 illustrates the classification of ALL, MLL and AML based on gene expression profile through a plot showing the error rate in class prediction using a cross-validation approach. One sample was withheld, and the class membership of this sample predicted based on gene expression levels. The genes used are the top 1–250 genes that are best correlated with the ALL/MLL/AML three-class distinction.

The class predictor was performed using a cross-validation approach and the K-Nearest Neighbors (K-nn) algorithm as follows. The k-nearest neighbors (k-NN) algorithm predicts the class of a new sample by calculating the Euclidean distance of the new sample to samples in a training set whose location has been identified in expression space. The predicted class of the new sample is then determined by identifying the class to which the majority of the k-nearest neighbors belong. The genes used to determine the location in expression space of each sample were identified by determining which genes best correlated with the class distinction as described above using the signal to noise statistic. For all experiments k=5. The prediction results shown in FIG. 6 were done using a cross validation approach where 1 of the 57 samples was withheld, the genes that best correlated with the ALL/MLL/AML distinction were determined, and those genes were used to build the k-nn algorithm. This was done for anywhere from 1–250 genes and the error rate (number of failures/57) is graphed vs. the number of genes. For the test set samples, the model was built with the 57 train set samples and then the class membership was determined for each "test sample" by determining the samples "neighbors" in gene expression space as described above.

Principal component analysis was performed using S-plus statistical software and the default settings. A commonly used technique for data reduction and visualization is principal component analysis (PCA). In this type of analysis, the linear combinations of variables are identified as the principal components that explain the variability in the dataset. To reduce the dimensionality of the data, the top 2 or 3 components can be graphed. In our case, the top 3 principal were thus used to project the samples in 3-dimensional space based on the gene expression profile. We first performed the analysis using the 8700 genes that passed the filtering described above. PCA was then performed using the top 500 genes that correlated with the AML/ALL class distinction. ALL, MLL, AML samples were then projected in that 500 gene space. These analysis were performed using S-plus statistical software using the default settings and covariance, followed by a three dimensional scatter plot of the coordinates of the 3 principal components for each sample. Singular value decomposition was used to derive the eigen values of the covariance matrix for the 8700 gene analysis. The S-Plus function used was "princomp( )". The coordinates of the three principal components for each sample were then used to project the samples in three dimensions.

Results

MLL is Distinct from ALL

To further define the biological characteristics specified by MLL translocations, gene expression profiles of leukemic cells from patients diagnosed with acute lymphoblastic leukemia bearing an MLL translocation were compared with conventional ALL which lack this translocation. Initially, samples from 20 patients with childhood ALL (denoted ALL), and 17 patients with MLL translocation (referred to as MLL) were collected. Patient details are presented in Table 1 (MLL) and Table 2 (ALL).

TABLE 1

MLL Patient Data

Figure 5:
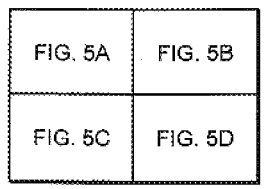
FIG. 5 provides a key depicting how
Figure 5A:
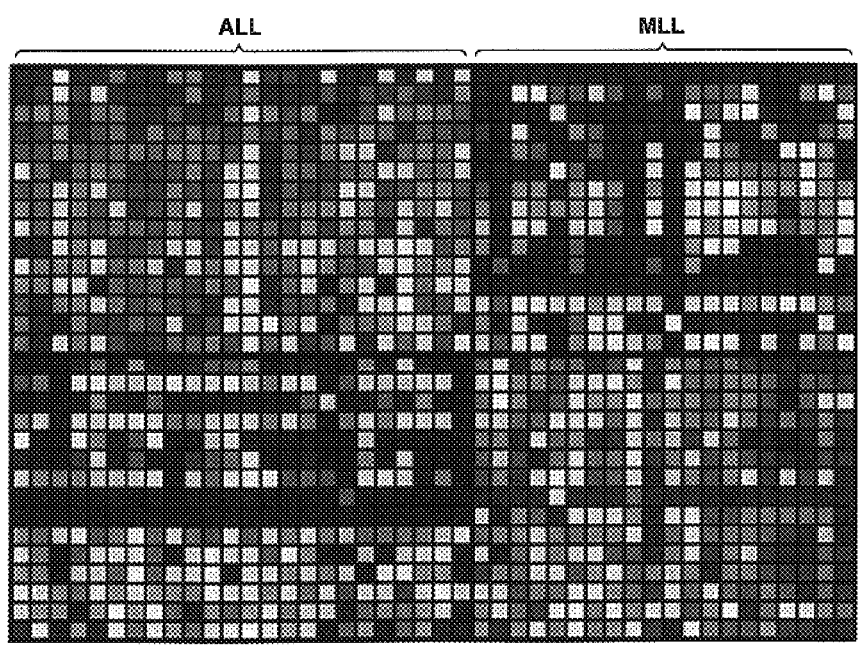
FIGS. 5A–5D are assembled to produce a complete figure.
Figure 5B:
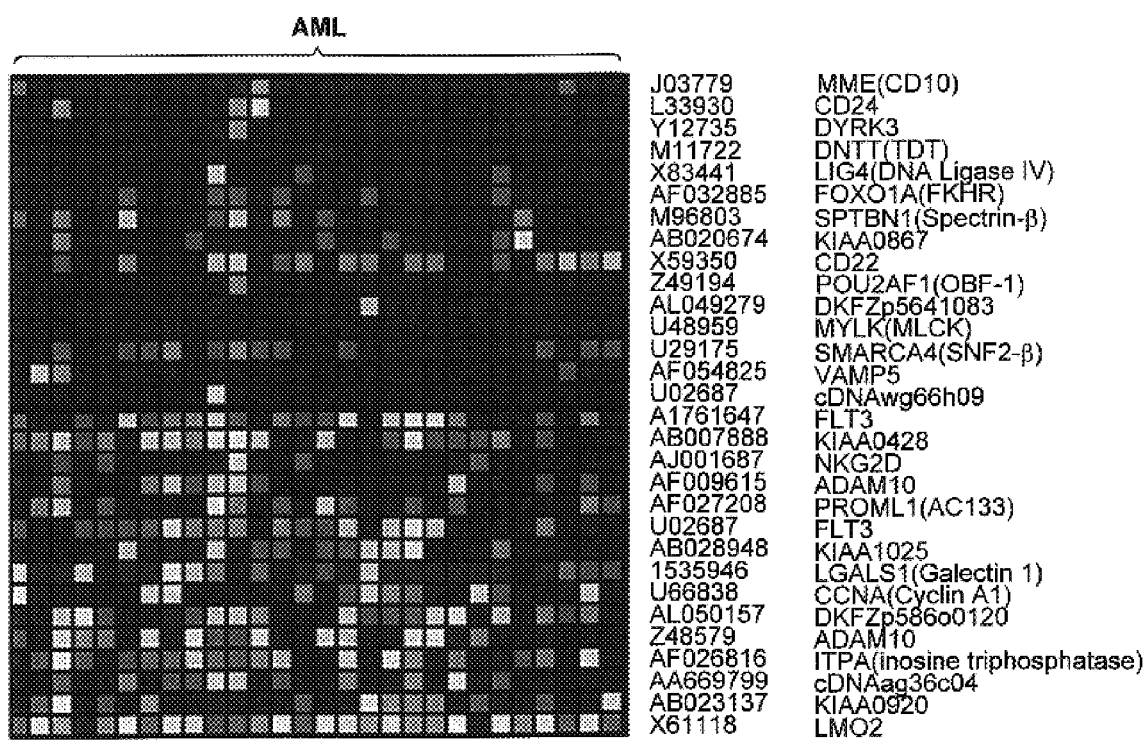
Figure 5C:
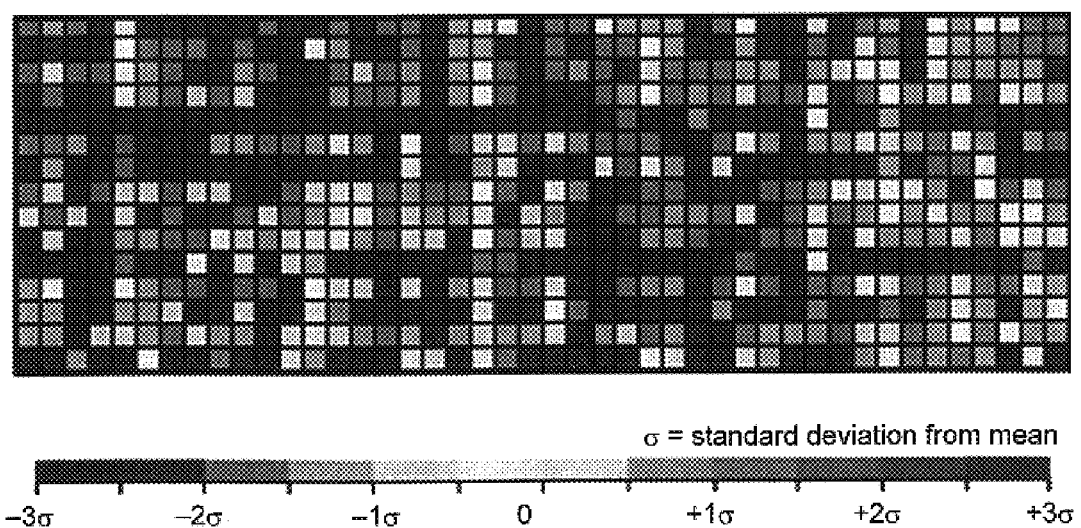
Figure 5D:
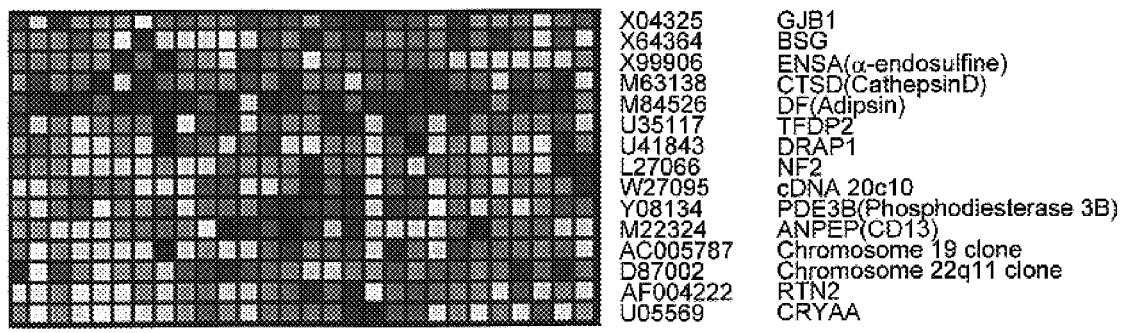

| Patient | Chromosome | Sample | Age at Diagnosis | Specimen | FIG./Column (MLL) |
|---|---|---|---|---|---|
| MLL_1 | t(4;11) | BM | 1 month | Diagnostic | FIG. 1&5 Column 1 |
| MLL_2 | So.Blot +# | BM | 3 months | Relapse | FIG. 1&5 Column 2 |
| MLL_3 | t(4;11) | PB | 8 months | Diagnostic | FIG. 1&5 Column 3 |
| MLL_4 | FISH +* | PB | 2 months | Relapse | FIG. 1&5 Column 4 |
| MLL_5 | FISH + | BM | 2 months | Diagnostic | FIG. 1&5 Column 5 |
| MLL_6 | FISH + | PB | 18 months | Diagnostic | FIG. 1&5 Column 6 |
| MLL_7 | t(4;11) | BM | 8 months | Relapse | FIG. 1&5 Column 7 |
| MLL_8 | t(4;11) | PB | 5 months | Diagnostic | FIG. 1&5 Column 8 |
| MLL_9 | So.Blot + | PB | 7 months | Diagnostic | FIG. 1&5 Column 9 |
| MLL_10 | t(1;11) | PB | 1 month | Diagnostic | FIG. 1&5 Column 10 |
| MLL_11 | t(3;11) (q13;q23) | PB | 1 day | Diagnostic | FIG. 1&5 Column 11 |
| MLL_12 | t(11;19) | BM | 3 months | Relapse | FIG. 1&5 Column 12 |
| MLL_13 | t(4;11) | PB | 1 month | Diagnostic | FIG. 1&5 Column 13 |
| MLL_14 | t(11;19) | BM | 3 months | Diagnostic | FIG. 1&5 Column 14 |
| MLL_15 | t(11;19) | PB | 7 months | Diagnostic | FIG. 1&5 Column 15 |
| MLL_16 | t(4;11) | PB | >21 years | Diagnostic | FIG. 1&5 Column 16 |
| MLL_17 | t(4;11) | PB | >21 years | Diagnostic | FIG. 1&5 Column 17 |
| MLL_18 | FISH + | PB | 10 months | Diagnostic | FIG. 5 Column 18 |
| MLL_19 | t(9;11) | PB | 4 years | Diagnostic | FIG. 5 Column 19 |
| MLL_20 | t(4;11) | PB | 6 years | Diagnostic | FIG. 5 Column 20 |

PB = peripheral blood
BM = bone marrow

TABLE 2

ALL Patient Data

| Patient | Tel/AML1 | Chromosomes | Sample | Age at Diagnosis | Specimen | FIG./Column (ALL) |
|---|---|---|---|---|---|---|
| ALL_1 | Pos. | 46 xy (+6) | BM | 6 y | Diagnostic | FIG. 1&5 Column 1 |
| ALL_2 | Pos. | Diploid | BM | 5 y | Diagnostic | FIG. 1&5 Column 2 |
| ALL_3 | Pos. | No data | BM | 4 y | Diagnostic | FIG. 1&5 Column 3 |
| ALL_4 | Pos. | Hyper-diploid, del7q | PB | 12 y | Diagnostic | FIG. 1&5 Column 4 |
| ALL_5 | Pos. | Hyper-diploid, del7q | BM | 12 y | Relapse | FIG. 1&5 Column 5 |
| ALL_6 | Pos. | Add 1p36, del 12p | BM | 4 y | Diagnostic | FIG. 1&5 Column 6 |
| ALL_7 | Pos. | Diploid | BM | 2 y | Diagnostic | FIG. 1&5 Column 7 |
| ALL_8 | Pos. | No Data | BM | 3 y | Diagnostic | FIG. 1&5 Column 8 |
| ALL_9 | Neg. | Diploid | BM | 9 y | Diagnostic | FIG. 1&5 Column 9 |
| ALL_10 | Neg. | Del 3p, Add 12p, Add 17q | BM | 5 y | Diagnostic | FIG. 1&5 Column 10 |
| ALL_11 | Neg. | del 12p13 | BM | 20 m | Relapse | FIG. 1&5 Column 11 |
| ALL_12 | Neg. | Hyperdiploid | BM | 13 m | Diagnostic | FIG. 1&5 Column 12 |
| ALL_13 | Neg. | Hyperdiploid | PB | 4 y | Relapse | FIG. 1&5 Column 13 |
| ALL_14 | Neg. | Diploid | BM | 20 m | Diagnostic | FIG. 1&5 Column 14 |
| ALL_15 | Neg. | Diploid | BM | 10 y | Diagnostic | FIG. 1&5 Column 15 |
| ALL_16 | Neg. | Diploid | BM | 4 y | Diagnostic | FIG. 1&5 Column 16 |
| ALL_17 | Neg. | Del 9p21 | PB | 11 y | Diagnostic | FIG. 1&5 Column 17 |
| ALL_18 | Neg. | Failed (MLL FISH Neg.) | PB | 15 y | Diagnostic | FIG. 1&5 Column 18 |
| ALL_19 | Neg. | Hyperdiploid | BM | 23 m | Diagnostic | FIG. 1&5 Column 19 |
| ALL_20 | Neg. | Diploid | BM | 9 y | Diagnostic | FIG. 1&5 Column 20 |
| ALL_21 | Neg. | Failed (MLL FISH Neg.) | PB | 12 m | Diagnostic | FIG. 1&5 Column 21 |
| ALL_22 | Neg. | t(1;19) | PB | 7 y | Diagnostic | FIG. 5 Column 22 |
| ALL_23 | Pos. | Diploid | PB | 3 y | Diagnostic | FIG. 5 Column 23 |

TABLE 2-continued

ALL Patient Data

| Patient | Tel/AML1 | Chromosomes | Sample | Age at Diagnosis | Specimen | FIG./ Column (ALL) |
|---|---|---|---|---|---|---|
| ALL_24 | Pos. | No Data | BM | 8 y | Diagnostic | FIG. 5 Column 24 |

Pos. = positive for TelAML1 translocation
Neg. = negative for TelAML1 translocation
PB = peripheral blood
BM = bone marrow
m = months
y = years First, it was determined if there were genes among the 12,600 tested whose expression pattern correlated with the presence of an MLL translocation. The genes were sorted by their degree of correlation with the MLL/ALL distinction (FIGS. 1A–1F), and permutation testing was used to assess the statistical significance of the observed differences in gene expression (Golub et al., *Science* 286:531–537 (1999)). For the 37 samples tested, approximately 1000 genes proved underexpressed in MLL as compared to conventional ALL while approximately 200 genes were relatively highly expressed. The top half of FIG. 1 shows the top 50 genes that are relatively underexpressed in MLL, and the bottom half of FIG. 1 shows the bottom 50 genes that are relatively overexpressed in MLL. Genes, and their GenBank Accession Numbers, are labeled at the right. The top 200 genes that make the ALL/MLL distinction and their GenBank Accession Numbers can be found in Table 3 (top 100 genes that are underexpressed in MLL compared to ALL) and Table 4 (top 100 genes that are overexpressed in MLL compared to ALL).

TABLE 3

Genes Underexpressed in MLL Compared to ALL

| GenBank No. | Name |
|---|---|
| J03779 | CD10 |
| AL050105 | DKFZp586H0519 |
| L33930 | CD24 |
| Y12735 | Dyrk3 |
| AB020674 | KIAA0867 |
| D26070 | ITPR3 |
| M11722 | TdT |
| M61877 | a-spectrin |
| X59350 | CD22 |
| W25798 | cDNA 13f12 |
| AL049279 | DKFZp564I083 |
| AF032885 | FKHR |
| L46922 | FHIT |
| S67427 | myosin |
| AL079277 | Unknown cDNA |
| M96803 | b-spectrin |
| X83441 | DNA Ligase IV |
| X15357 | ANP-receptor |
| M55284 | Protein Kinase C-L |
| AI146846 | cDNA qb92h04 |
| AB023176 | KIAA0959 |
| AF002999 | TRF2 |
| D26070 | ITPR3 |
| Y11312 | PI3-Kinase |
| U48959 | MLCK |
| J05243 | a-spectrin |
| Y14768 | Cosmid TN62 |
| U01062 | ITPR3 |
| Z49194 | OBF-1 |

TABLE 3-continued

Genes Underexpressed in MLL Compared to ALL

| GenBank No. | Name |
|---|---|
| V59423 | Smad1 |
| U29175 | Snf2-b |
| M81141 | HLA-DQ-b |
| D87437 | KIAA0250 |
| Y00264 | Amyloid A4 precursor |
| U59912 | Smad1 |
| AJ007583 | acetylglucosaminyltransferase |
| L75847 | ZNF-45 |
| D17530 | Dreberin E |
| D86967 | KIAA0212 |
| J03600 | Lipoxygenase |
| D42055 | KIAA0093 |
| AL021154 | Chromosome 1 PAC |
| AI761647 | cDNA wg66h09 |
| AF054815 | VAMP5 |
| N36926 | cDNA YY38E04 |
| U96113 | Nedd-4-like ubiquitin ligase |
| AB019527 | LDOC1 |
| M34641 | FGF Receptor-1 |
| L29376 | MHC class I mRNA |
| M60028 | HLA-DQ-b |
| AA808961 | cDNA nw16h03.s1 |
| AB018303 | KIAA0760 |
| X74837 | HUMM9 |
| AL022723 | Chromosome 6 sequence |
| M74719 | E2-2 |
| M63838 | IFI16 |
| U81607 | Gravin |
| U96113 | Nedd-4 like ubiquitin ligase |
| D13639 | KIAK0002 |
| X53586 | Integrin alpha 6 |
| U01062 | ITPR3 |
| M21535 | ERG11 |
| D88827 | Zinc finger protein FPM315 |
| W26406 | cDNA 29b7 |
| U15642 | E2F-5 |
| D43949 | KIAA0082 |
| J011001 | TM7XN1 |
| M63928 | CD27 |
| AB028961 | KIAA1038 |
| X55740 | 5'Nucleotidase |
| L05186 | Focal adhesion kinase |
| AF070588 | cDNA 24554 |
| U48705 | Tyrosine Kinase DDR |
| AF070614 | cDNA 24732 |
| U23850 | ITPR3 |
| AF054180 | Hematopoietic zinc finger protein |
| AL049471 | DKFZp586N012 |
| AF084481 | WFS1 |
| U90547 | Human Ro |
| U15085 | HLA-DMB |
| AJ001381 | cDNA for an allele of |

TABLE 3-continued

Genes Underexpressed in MLL Compared to ALL

| GenBank No. | Name |
|---|---|
|  | myosin |
| AL049933 | DKFZp564K1216 |
| AI198311 | cDNA qi61f11.x1 |
| AL050060 | DKFZp566H073 |
| X06318 | PKC-b1 |
| U43885 | Grb2-associated binder-1 |
| M31523 | E2A transcription factor |
| L10373 | clone CCG-B7 |
| Y11306 | TCF-4 |
| X05323 | MRC OX-2 gene |
| X78932 | Zinc finger protein HZF9 |
| W26633 | cDNA 34b1 |
| AF052131 | clone 23930 |
| AL050260 | DKFZp564E1082 |
| AL080218 | DKFZp586N1323 |
| A1561196 | cDNA tq27a01.x1 |
| W26023 | cDNA 18c3 |
| U68186 | Extracellular matrix I |
| X62744 | RING6 |
| X78926 | Zinc Finger HZF3 |

TABLE 4

Genes Overexpressed in MLL Compared to ALL

| GenBank No. | Name |
|---|---|
| AI535946 | Lectin HL14 |
| M14087 | Lectin HL14 |
| AI201310 | cDNAqf71b11 |
| M80899 | AHNAK |
| AJ001687 | NKG2D |
| U66838 | Cyclin A1 |
| M59040 | CD44 |
| M95929 | Phox1 |
| D25217 | KIAA0027 |
| AI597616 | cDNAtn15f08 |
| W72186 | cDNAzd69b10 |
| U41813 | HOXA9 |
| L05424 | CD44 |
| L05424 | CD44 |
| AC004080 | Chromosome 7 PAC |
| X05908 | Annexin I |
| U78027 | chromosome X BAC |
| Y00062 | CD45 |
| AF098641 | CD44 |
| Y000638 | CD45 |
| AF004230 | monocyte elastase inhibitor |
| W60864 | cDNAzd27g05 |
| X55989 | Eosinophil CRP |
| M93056 | Monocyte MIR-7 |
| AF027208 | AC133 |
| Z83844 | Chromosome 22 sequence |
| AL050396 | DKFZp586K1720 |
| AA978353 | cDNAoq40b07 |
| D21261 | KIAA0120 |
| L08177 | EBV induced EBI2 |
| L19182 | MAC25 |
| D28364 | Annexin II |
| D15057 | DAD-1 |
| AF020044 | C-type lectin precursor |
| AI138834 | cDNAqe04b02 |
| X73882 | E-MAP-115 |
| AF026816 | Putative Oncogene |
| X17042 | Proteoglycan I |
| M20867 | glutamate dehydrogenase |
| U60060 | FEZ1 |
| AF025529 | LIR-6 |
| AB007888 | KIAA0428 |
| M13485 | Metallothionein I-B |
| M26679 | HOX A5 |
| AL050267 | DKFZp564A032 |

TABLE 4-continued

Genes Overexpressed in MLL Compared to ALL

| GenBank No. | Name |
|---|---|
| R92331 | cDNA03h03 |
| AL050162 | DKFZp586B2022 |
| AI017574 | cDNAou23f10 |
| M62896 | Annexin II |
| AL050374 | DKFZp586c1619 |
| U67516 | MAPKKK5 |
| AF072099 | Immunoglobulin-like transcript 3 |
| X96753 | chondroitin sulfate proteoglycan NG2 |
| X52075 | CD43 |
| U38545 | Phospholipase I |
| D00017 | Annexin II |
| U02687 | FLT-3 |
| AA570193 | cDNAnf38c11.s1 |
| U21551 | ECA39 |
| X55988 | eosinophil derived neurotoxin |
| D78177 | quinolinate phosphoribosyl transferase |
| Z48579 | disintegrin-metalloprotease |
| AF039656 | NAP-22 |
| Y00638 | CD45 |
| J03910 | Metallothionein-IG |
| AF030339 | VESPR |
| M28713 | NADH-cytochrome B5 reductase |
| AB023209 | KIAA0992 |
| L40377 | CAP2 |
| D86181 | galactocerebrosidase |
| M83215 | AML1 |
| X61118 | LMO2 |
| U01147 | ABR |
| M96995 | GRB2 |
| AF040704 | putative tumor suppressor (101F6) |
| U57971 | calcium ATPase |
| AB028948 | KIAA1025 |
| U11791 | cyclin H |
| AF022991 | Rigui |
| L11669 | Tetracycline-like transporter |
| U39064 | MAPKK6 |
| AF054176 | Angiotensin |
| U87947 | HNMP-1 |
| L19872 | AH-receptor |
| M36035 | benzodiazepine receptor |
| U93305 | Chromosome X p11 sequence |
| AF009615 | ADAM10 |
| X52541 | EGR1 |
| AF044253 | potassium channel beta-2 |
| M26683 | Interferon gamma inducible mRNA |
| M31166 | TSG-14 |
| R93527 | cDNAyq35f10.r1 |
| X15998 | chondroiton sulfate proteoglycan |
| X55990 | eosinophil cationic protein |
| U73960 | ARF-like protein 4 |
| M13452 | Lamin A |
| AI560890 | cDNA tq41d05.x1 |
| AB024057 | vascular rab-gap |
| M97815 | CRABP-II |
| M60614 | WIT-1 |

As shown in FIGS. 1A–1F and Tables 1 and 2, MLL shows a dramatically different gene expression profile from ALL.

MLL Shows Multi-lineage Gene Expression

Figure 1B:
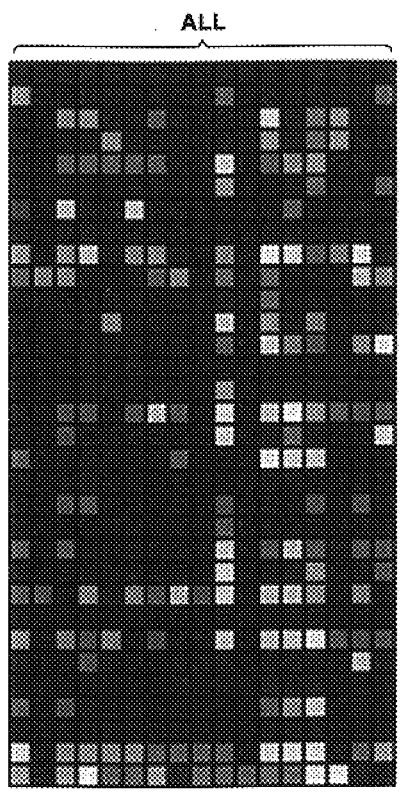
Figure 1C:
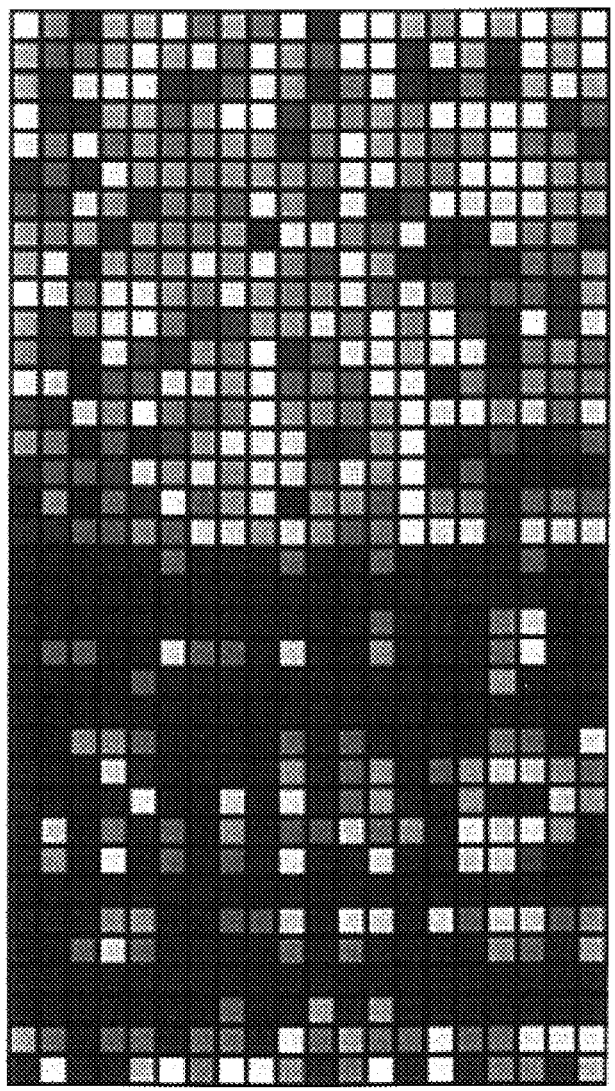
Figure 1E:
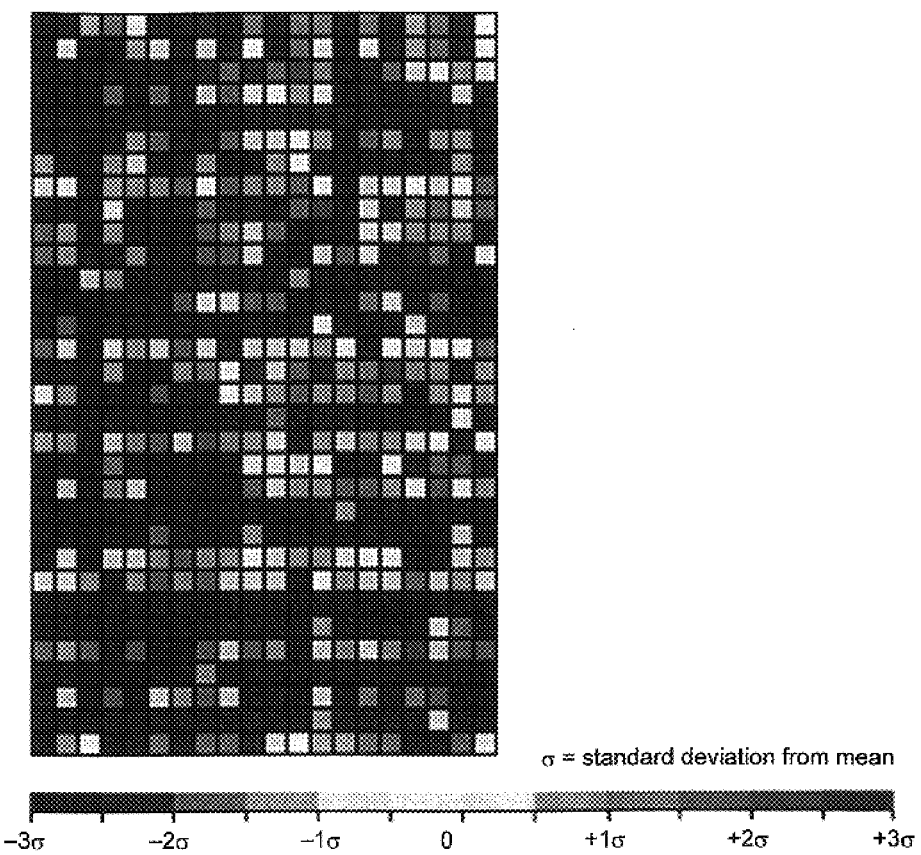

Inspection of the genes differentially expressed between MLL and ALL was instructive (FIGS. 1A–1F and Tables 1 and 2). Many underexpressed genes in MLL have a function in early B cell development. These include genes expressed in early B-cells (CD 10, CD24, CD22, TdT) (Hardy and Hayakawa, Annu Rev immunol., 19:595–621 (2001); LeBien, Blood 96:9–23 (2000)), genes required for appropriate B-cell development (E2A, E2-2, P13-Kinase, Octamer Binding Factor-1, and DNA ligase IV) (Murre, *Cold Spring Barb Symp Quant Rio* 164:39–44 (1999); Fruman et at., Science 283:393–397 (1999); Schubart et al., Nat Immunol 2:69–74 (2001); and Frank et at., *Nature* 396:173–177 (1998)), and genes found to be correlated with B-precursor ALL in an AML/ALL comparison (Snj2-β) (Golub et al., *Science* 286:531–537 (1999)). The relative underexpression of the forkhead (FKHR), SMADI and TCF-4 transcription factors suggests they may also be involved in later stages of B-cell differentiation or leukemogenesis. Relatively overexpressed genes in MLL include the adhesion molecules HL14, Anntexin I, Annexin II, CD44, and CD43. Multiple genes that are expressed in hematopoictic lineages other than lymphocytes are also highly expressed in MLL. These include genes expressed in progenitors (AC133, FLT3, LM02) (Yin et al., Blood 90:5002–5012 (1997); Rosnet et al., Blood 82:1110–1119 (1993); and Dong et al., Br J Haematol 93:280–286 (1996)), myeloid specific genes (Cyclin A1, monocyte elastase inhibitor, macrophage capping protein, eosinophil-CRP), (Yang et al., Blood 93:2067–2074 (1999); Remold-O'Donnell et al., Proc Natl Acad Sci USA 89:5635–5639 (1992); and Rosenberg et al., J Exp Med. 170:163–176 (1989)), and at least one natural killer cell specific gene (NKG2D) (Ho et al., Proc Natl Acad Sci USA, 95:6320–6325 (1998)) (FIGS. 1A, 1B and Tables 1 and 2). Overexpression of HOXA9 and Proteoglycan I in MLL is of particular interest as these genes were previously reported to be highly expressed in AML (Golub et al., Science 286:531–537 (1999)), and overexpression of HOXA9 has been associated with a poor prognosis (Golub et al., Science 286:531–537 (1999)).

MLL is Arrested at an Early Stage of Hematopoietic Development

Figure 2A:
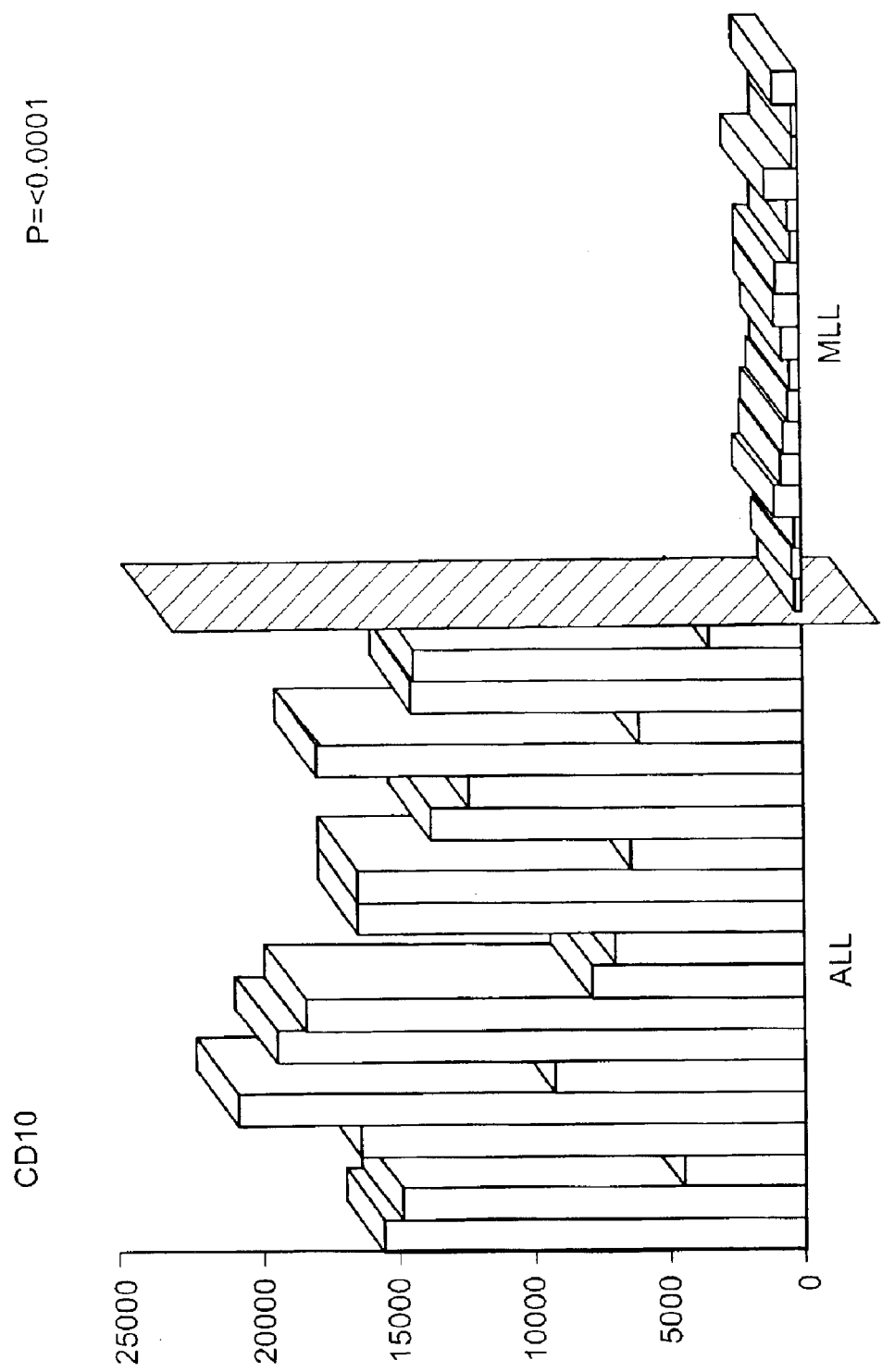
FIG. 2A illustrates selected early lymphocyte gene expression in ALL and MLL. Relative levels of expression of CD10 in ALL and MLL samples are shown. Each bar represents an individual leukemia sample. The expression values are raw data obtained from Affymetrix GENECHIP® analysis after scaling of the arrays based on the scaling described in the Examples.
Figure 2B:
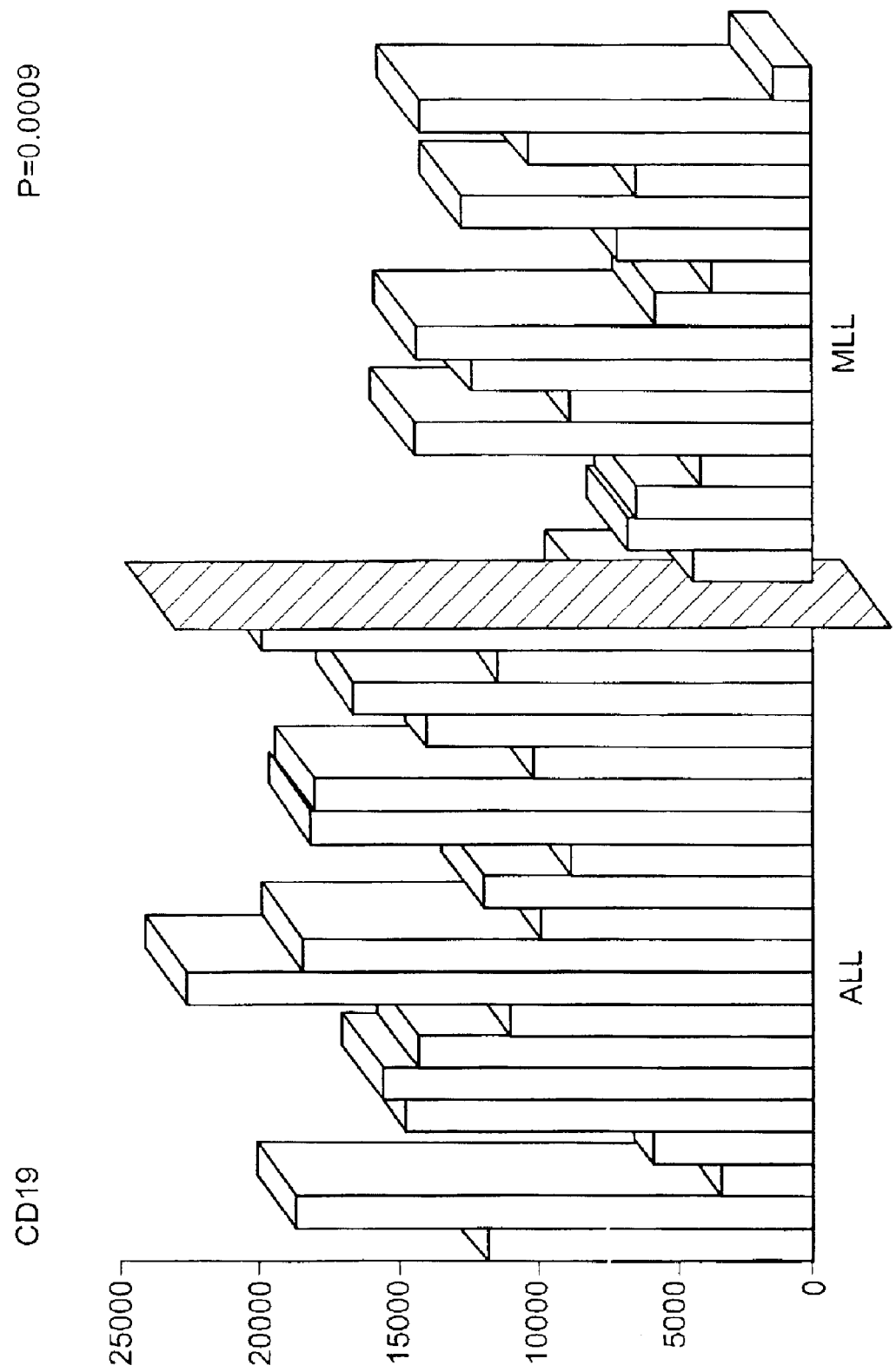
FIG. 2B illustrates selected early lymphocyte gene expression in ALL and MLL. Relative levels of expression of CD19 in ALL and MLL samples are shown. Each bar represents an individual leukemia sample. The expression values are raw data obtained from Affymetrix GENECHIP® analysis after scaling of the arrays based on the scaling described in the Examples.
Figure 2C:
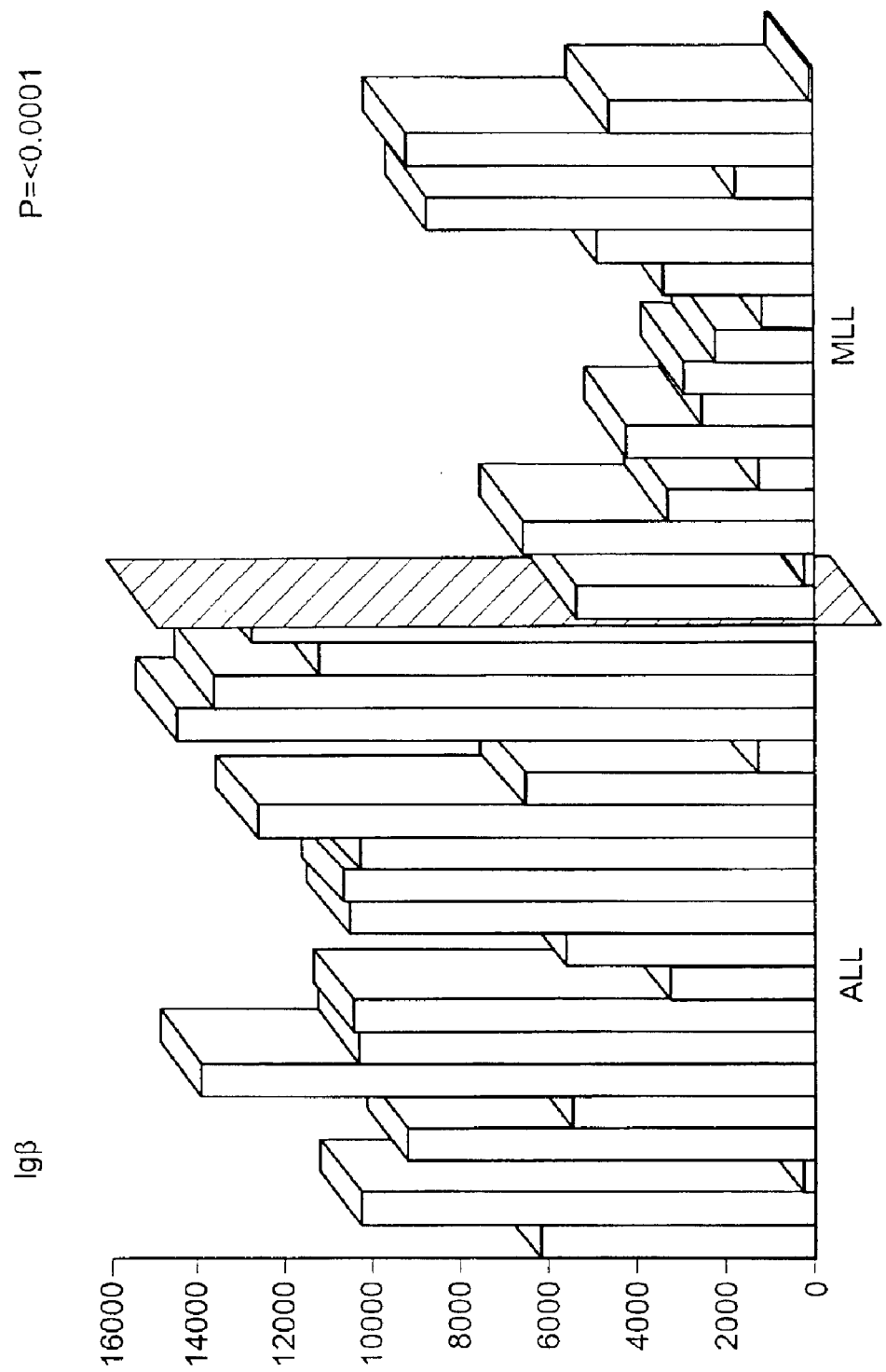
FIG. 2C illustrates selected early lymphocyte gene expression in ALL and MLL. Relative levels of expression of IgB in ALL and MLL samples are shown. Each bar represents an individual leukemia sample. The expression values are raw data obtained from Affymetrix GENECHIP® analysis after scaling of the arrays based on the scaling described in the Examples.

Since lymphoblasts with MLL rearrangement express many myeloid specific genes, a detailed assessment of the expression of lymphoid genes was performed. Genes known to mark early B-lymphoid commitment such as Igβ and CD19 are expressed in MLL albeit at lower levels than in ALL (FIGS. 2C and 2B). CD10 (CALLA) is not expressed in MLL (FIG. 2A), whereas the IL-7 receptor is expressed at similar levels in ALL and MLL.

Figure 2E:
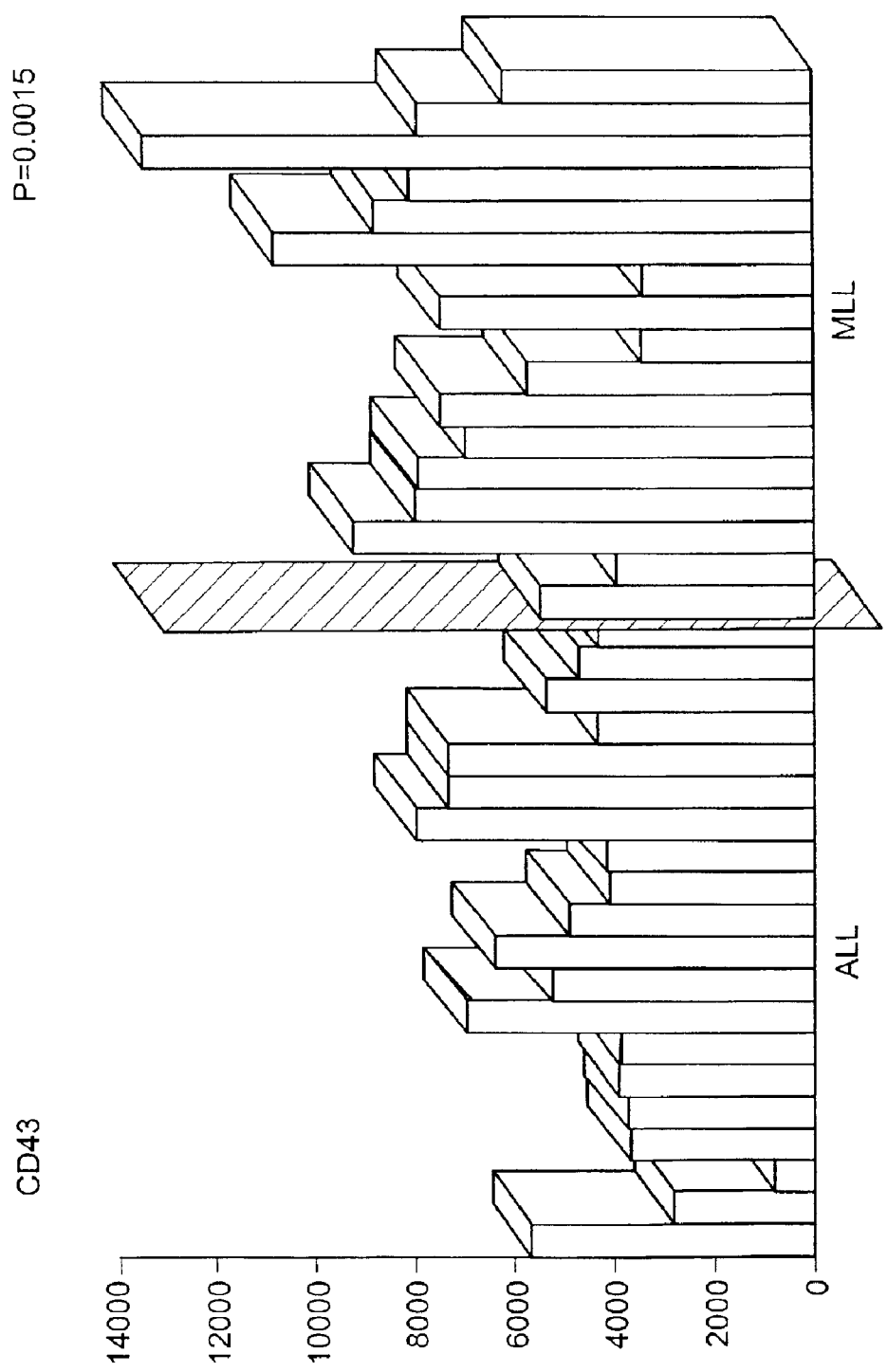
FIG. 2E illustrates selected early lymphocyte gene expression in ALL and MLL. Relative levels of expression of CD43 in ALL and MLL samples are shown. Each bar represents an individual leukemia sample. The expression values are raw data obtained from Affymetrix GENECHIP® analysis after scaling of the arrays based on the scaling described in the Examples.
Figure 2F:
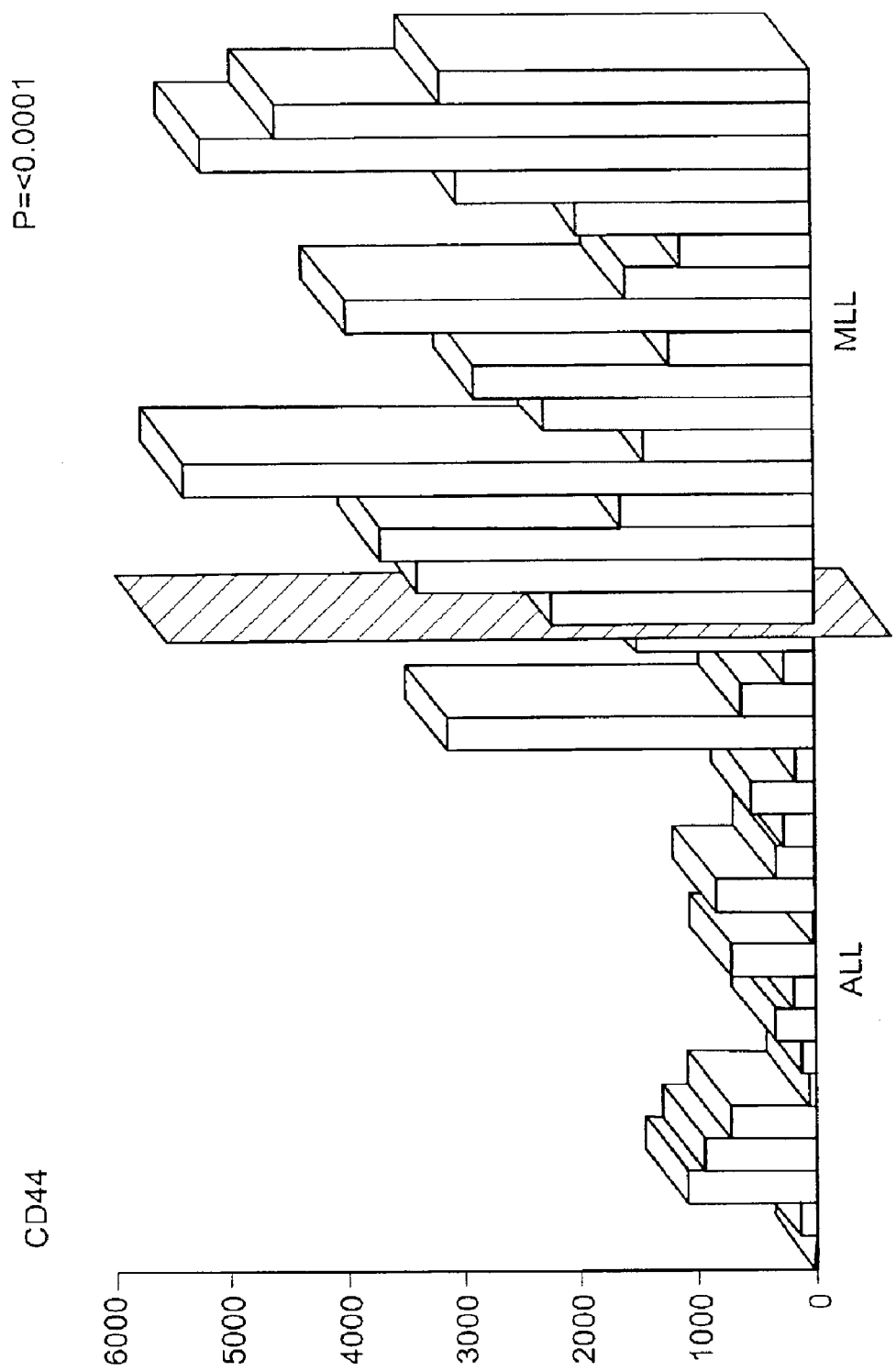
FIG. 2F illustrates selected early lymphocyte gene expression in ALL and MLL. Relative levels of expression of CD44 in ALL and MLL samples are shown. Each bar represents an individual leukemia sample. The expression values are raw data obtained from Affymetrix GENECHIP® analysis after scaling of the arrays based on the scaling described in the Examples.

A number of genes have been shown to vary their expression level as murine hematopoietic cells transition from stem cell, to common lymphoid progenitor, to pro-B and then pre-B cells. Igβ, CD24, CD44 and CD43 represent early steps of lymphoid development (Hardy and Hayakawa, *Annu Rev Immunol* 19:595–621 (2001) and Kondo et al., Cell 91:661–672 (1997)). Igβ and CD24 expression increases with maturation while CD44 and CD43 levels decrease (Kondo et al., Cell 91:661–672 (1997)). The MLL samples express relatively low levels of CD24 and Igβ but high levels of both CD44 and CD43 (FIGS. 2F and 2E). In total these data suggest that MLL represents a maturational arrest at an early lymphoid progenitor stage of development.

Selected HOX Genes are Highly Expressed in MLL Versus ALL

Figure 3B:
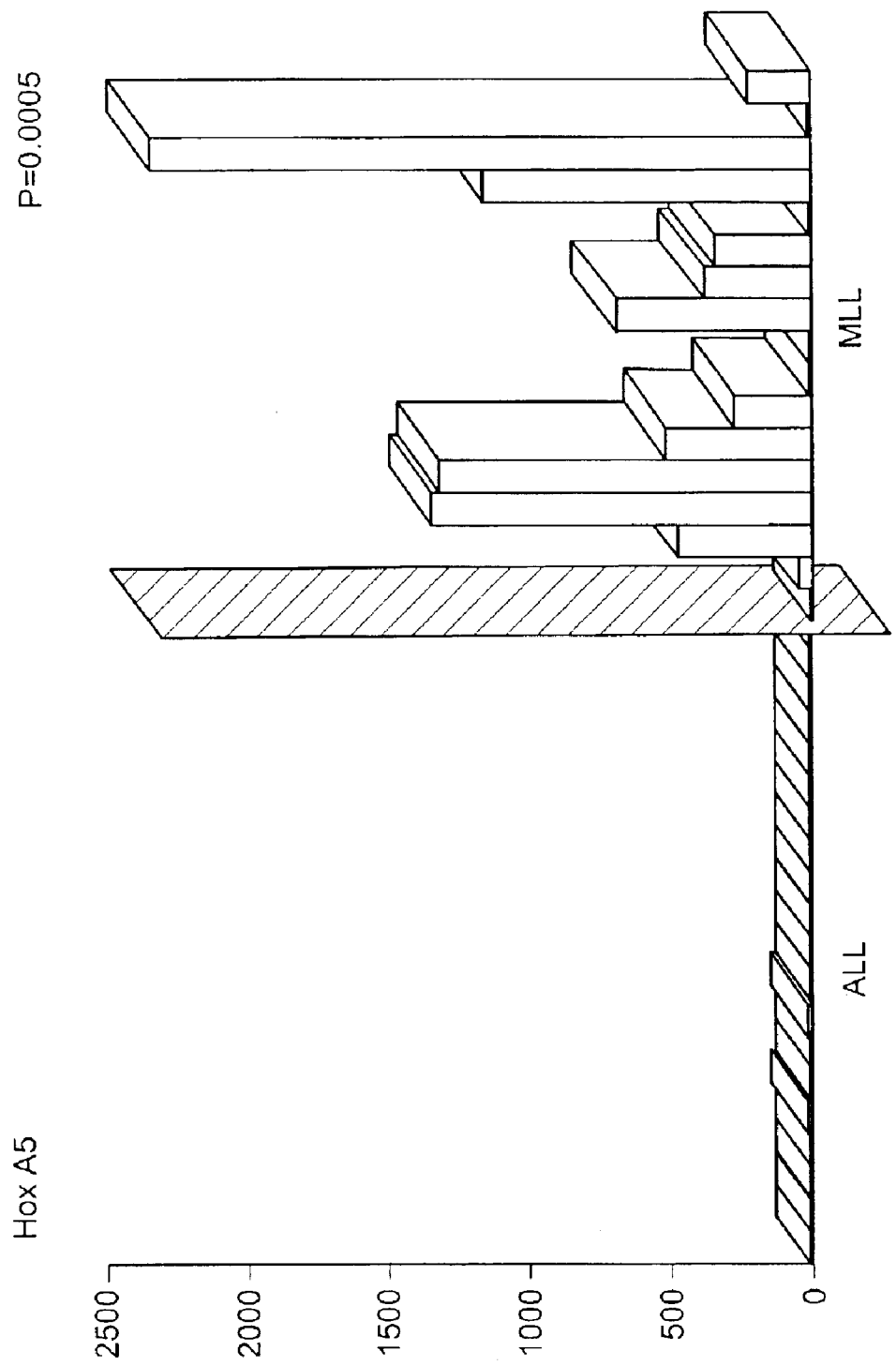
FIG. 3B illustrates selected HOXA5 gene expression in ALL and MLL. Relative levels of expression of HOXA5 in ALL and MLL samples are shown. The expression values are obtained using Affymetrix GENECHIP® analysis after scaling of the arrays as described in the Examples.
Figure 3C:
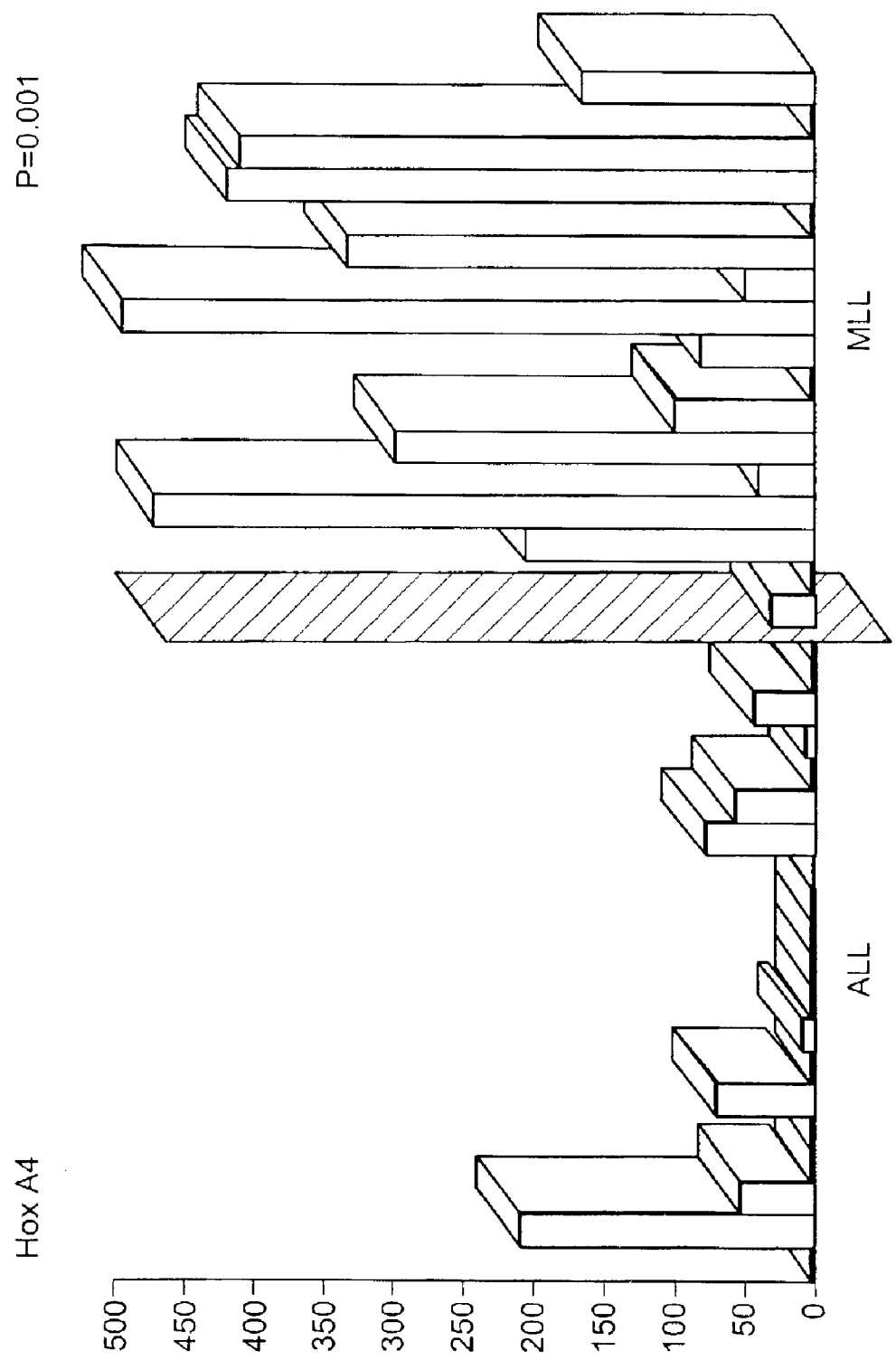
FIG. 3C illustrates selected HOXA4 gene expression in ALL and MLL. Relative levels of expression of HOXA4 in ALL and MLL samples are shown. The expression values are obtained using Affymetrix GENECHIP® analysis after scaling of the arrays as described in the Examples.
Figure 3D:
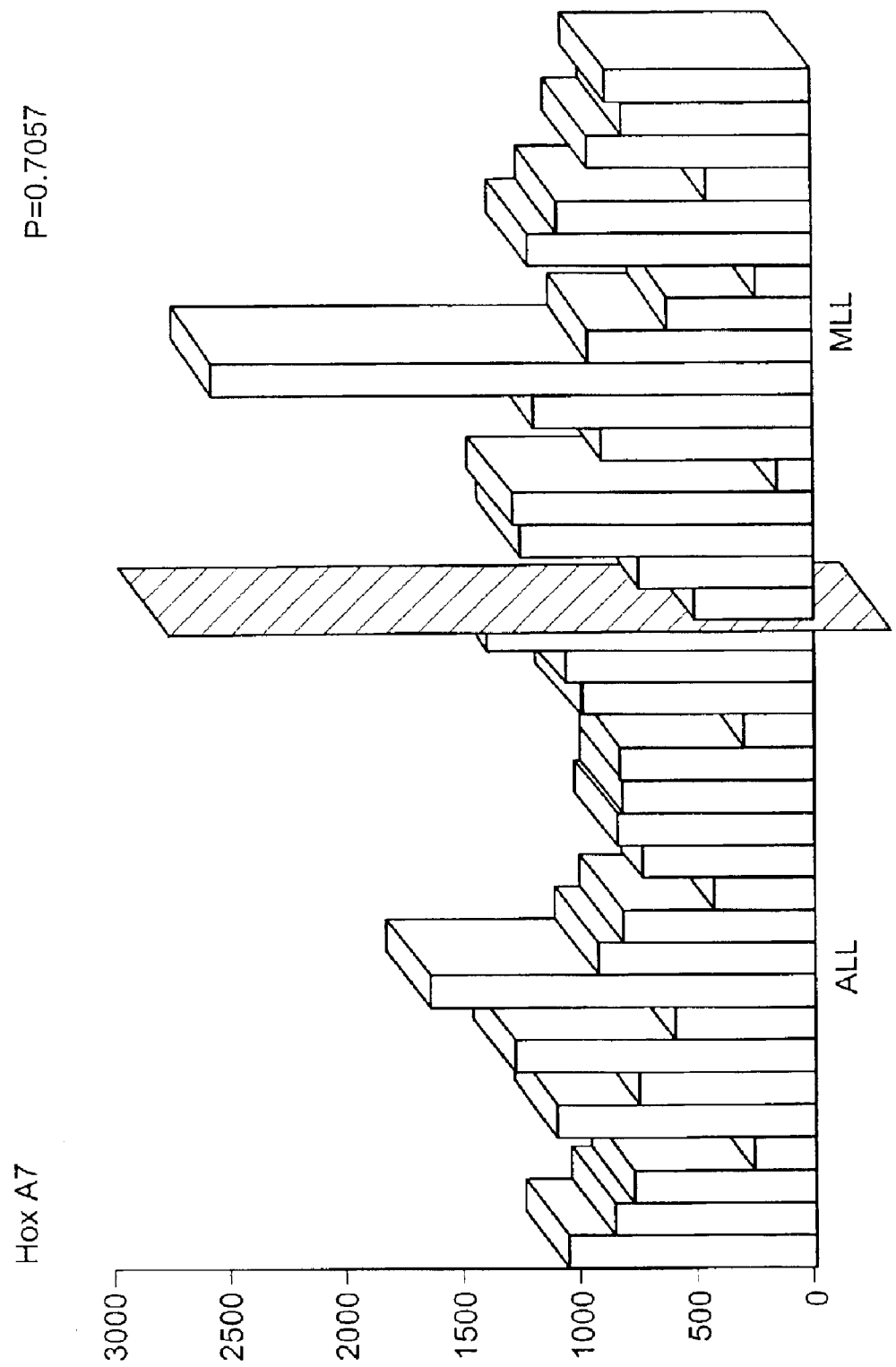
FIG. 3D illustrates selected HOXA7 gene expression in ALL and MLL. Relative levels of expression of HOXA7 in ALL and MLL samples are shown. The expression values are obtained using Affymetrix GENECHIP® analysis after scaling of the arrays as described in the Examples.

Multiple members of the class I Hox genes are known to be regulated by Mll (Yu et al., Nature 378:505–508 (1995)) prompting a detailed comparison of the patterns of HOX gene expression between ALL and MLL. Several of the 20 class I HOX genes present on the microarrays demonstrated significant and consistent differences in expression. HOXA9 and HOXA5 were not expressed in conventional ALL, but were expressed, often at high levels, in most MLL samples (FIGS. 3A–3D). Similarly, HOXA4 was typically expressed in MLL, but rarely in conventional ALL (FIG. 3C). HOXC6 showed mildly elevated levels of expression in MLL (Supplemental Information at http://research.dfci.harvard.edu/korsmeyer/MLL.htm). However, the HOX patterns displayed selectivity as other genes such as HOXA7 showed no obvious difference in their expression pattern (FIG. 3D). MEIS1, a cofactor for HOX proteins, which can accelerate HoxA9 dependent leukemia (Nakamura et al., Nat Genet 12:149–1531 (1996)), was also significantly overexpressed in MLL as previously reported for the t(4;11) containing subset (Rozovskaia et al., Oncogene 20:874–878 (2001)).

MLL is Distinct from Both AML and ALL

Figure 4B:
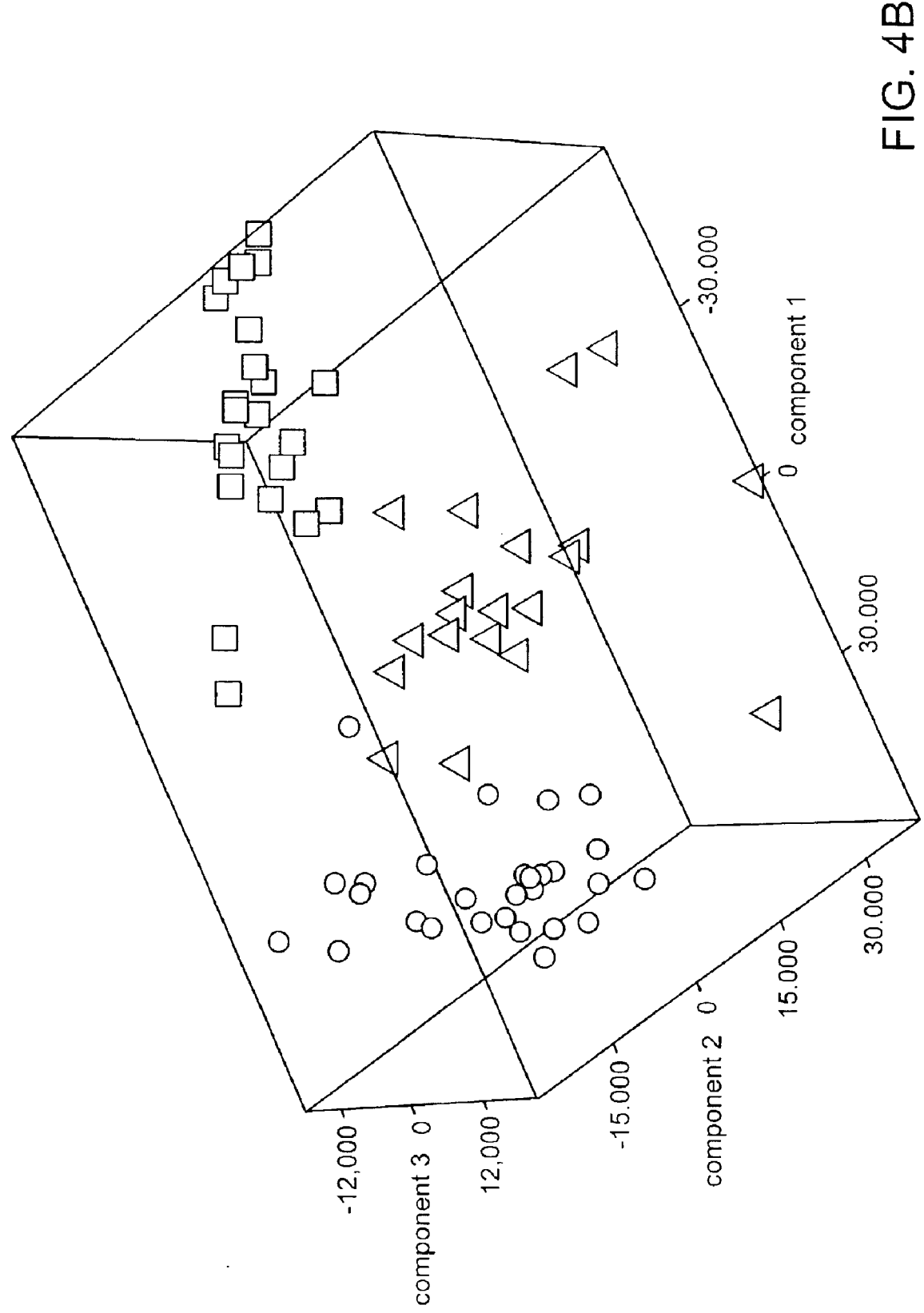
FIG. 4B illustrates the comparison of gene expression between ALL, MLL and AML, and shows the PCA plot comparing ALL (squares), MLL (triangles), and AML (circles) using the 500 genes that best distinguished ALL from AML.

MLL is characterized by the expression of myeloid specific genes, which raised the possibility that MLL is more closely related to acute myelogenous leukemia (AML). To determine if this is the case, or if MLL is separable as a distinct type of leukemia, a principal component analysis (PCA) was performed using the gene expression profiles of MLL, ALL and AML specimens. This clustering algorithm reduces complex multidimensional data to a few specified dimensions so that it can be visualized effectively (Venables and Ripley, Modern Applied Statistics with S-Plus, Springer Verlag, New York (1994)). First, the analysis was performed in an unsupervised manner using the 8700 genes that showed some variability in expression level. As expected, the ALL and AML samples displayed substantial separation (FIG. 4A). Of note, the MLL samples proved largely separate from either AML or ALL (FIG. 4A). In order to determine if this separation could be attributed to a difference in hematopoietic identity, a similar analysis was performed using the 500 genes whose expression best distinguished the separation of AML versus ALL. When projected into this 500-gene space using PCA the MLL samples principally fall between the AML and ALL samples (FIG. 4B).

Since the above clustering analyses supported three distinct entities of ALL, AML and MLL, it was queried if selected genes could be identified which distinguished each type of leukemia from the other two (FIGS. 5A–5D). Conventional ALL expressed high levels of the following genes compared to MLL and AML: CD10, CD24, DYRK, TdT, FKHR, DNA ligase IV, KIAA0867, CD22, OBF-1, B-spectrin, DKFZp5641083, Snf-2B, MLCK, VAMP5, and cDNA wg66h09) and these genes were underexpressed in MLL and ALL. AML samples expressed high levels of the following genes compared to ALL and MLL: adipsin, cathepsinD, CD 13, M6 antigen, gap junction protein, a-endosulfine, NF-2 transcription factor DP-2, DRAP1, cDNA 20c1, phosphodiesterase 3B, cosmid 19p 13.2, chromosome 19 clone, chromosome 22q11 clone, and CRYAA, and these genes were underexpressed in ALL and MLL. MLL samples expressed high levels of the following genes compared to ALL and AML: AC 133, LMO2, FLT3, KIAA0428, NKG2D, ADAM10, KIAA 1025, Lectin HL14, cDNA ag36c04, cyclin A1, ADAM10, putative oncogene, DKFZp585o01, KIAA0920, and LMO2, and these genes were underexpressed in ALL and AML. The GenBank Accession Numbers for each of these genes is shown in FIGS. 5A–5D. Permutation analysis indicated that approximately 200 genes were significantly overexpressed in MLL as compared to the other two leukemia categories. In combination, the PCA and gene expression comparisons (FIGS. 4A, 4B and 5A–5D) indicate that MLL is a separable, distinct disease based on gene expression profile. These data also show that ALL and AML are separable distinct diseases. The genes shown in FIGS. 5A–5D, particularly the genes that are over expressed in each disease type, can be used in gene expiession profile studies to diagnose MLL, ALL, or AML. These genes, including underexpressed and overexpressed genes for each disease type, can also be used as target for identifying and/or detecting compounds that alter expression and/or activity of these genes or their gene products, for therapeutic methods, and for monitoring efficacy of treatment, as described herein.

Gene Expression Profiles Correctly Classify ALL, MLL and AML

A more stringent assessment of the power of the aforementioned difference in gene expression profiles would be their capacity to assign individual samples as MLL, ALL, or AML. The detection of MLL translocations in leukemia samples is currently most often performed by either cytogenetic analysis or by fluorescence in situ hybridization (FISH) which can technically fail or may be unavailable. Thus, other approaches to correctly assign individual cases to meaningful subsets of leukemia would be useful. To test this possibility a three-class predictor was developed based on a k-nearest neighbors algorithm (Dasarathy (ed), IEEE Computer Society Press, Los Altos, Calif., December 1991. ISBN: 0818689307). This algorithm assigns a test sample to a class by identifying the k nearest samples in the training set and choosing the most common class among these k nearest neighbors. For this purpose, distances were defined by a euclidean metric based on the expression levels of a specified number of genes.

The accuracy of this method was assessed using a cross validation approach. When one of the 57 samples is removed, the genes that most closely correlate with the ALL/MLL/AML class distinction are identified, and the expression of these genes used to determine the class of the withheld sample. The model assigned the withheld sample to the appropriate class with 95% accuracy. Moreover this accuracy was maintained as we extended from 40 to 250 genes to build the predictor (FIG. 6), as further testimony to the strong distinction among these leukemia categories.

To assess if the unique signature of gene profiles in MLL samples could be attributed to their occurrence in infants, the above model was tested using 10 independent leukemia samples. The test set consisted of 3 childhood (>12 months) conventional ALLs, 2 lymphoblastic leukemias of childhood carrying cytogenetically verified MLL translocations, 2 infant (<12 months) leukemias in which cytogenetic analysis did not detect an MLL translocation and 3 AML samples. Utilizing the 100 genes that best correlated with the three-class distinction, nine of ten samples were correctly classified as MLL, ALL or AML. The one apparent error was an infant reported to be negative for an MLL rearrangement by cytogenetics, yet consistently predicted to have a rearrangement based on gene expression profile. This prompted further analysis by FISH, which confirmed that this infant leukemia did indeed possess an MLL translocation and that the prospective assignment by expression profiling was correct. Taken together these data show that the unique gene expression profile characteristic of MLL cannot be attributed merely to the fact that most samples are from infants.

Discussion

Gene expression profiles of lymphoblastic leukemias which possess an MLL translocation are remarkably consistent and differ significantly from those of other leukemias. Consequently, it is appropriate that they be considered a distinct disease entitled MLL for "Mixed Lineage Leukemia." This is supported by their comparison to conventional B cell precursor ALL that lacks MLL rearrangement, where ~1000 genes proved underexpressed and ~200 overexpressed in the MLL rearranged group. Moreover, evaluation of the expression profiles using principal component analysis indicated that MLL was clearly separable from conventional ALL and also AML. The expression differences are so robust that ~95% of leukemic samples were correctly classified as MLL, ALL or AML. As testimony to the extent of divergence of MLL, it remained separable from ALL and AML when 250 genes were used to build the class predictor. This provides strong evidence that a specific chromosomal translocation results in a distinct type of lymphoblastic leukemia, rather than a model in which all translocations merely provide transformation events that subsequently converge upon a common pathway of leukemogenesis. In addition, the data indicate that MLL is arrested at an earlier stage of differentiation and/or has a different cell of origin than ALL. Select Hox genes are overexpressed in ILL-dependent leukemia, as compared to normal B-cell progenitors and other ALL. FLT3 expression best distinguishes MLL from ALL.

Gene expression patterns of MLL provide insight into the proposed models for its cellular origin. A summary of expression profiles shows that MLL expresses some lymphocyte specific and myeloid specific genes, but at lower levels than either conventional ALL or AML, respectively. Based on murine studies that have defined gene expression patterns during lymphocyte commitment (Hardy and Hayakawa, Annu Rev Immunol 19:595–621 (2001); and Kondo et al., Cell 91:661–672 (1997)), the low-level expression of CD24 and Igβ, along with high expression of CD43 and CD44 suggests that MLL is arrested at an earlier stage of development than conventional ALL. Furthermore, the expression of genes typically found in progenitor cells suggests MLL represents an early hematopoietic progenitor. This is consistent with studies that have shown multi-lineage gene expression in hematopoietic progenitors prior to full lineage commitment (Hu et al., Genes Dev 11:774–785 (1997)). Of particular interest is the possibility that MLL may represent the expansion of a bipotential B-macrophage progenitor (Montecino-Rodriguez et al., Nat Immunol 2:83–88 (2001); and Cumano et al., Nature 356:612–615 (1992)). Early B-cells can be induced to differentiate into myelomonocytic cells under certain conditions (Nutt et al., Nature 401:556–562 (1999)), and derivation of macrophages from leukemia cell lines has been well documented (Borrello and Phipps, Immunol Today 17:471–475 (1996)). An attractive model would hold that the MLL-fusion protein drives the "transdifferentiation" of an early lymphocyte progenitor. The expression of many myeloid and monocyte/macrophage specific genes is consistent with MLL reflecting a very early B cell progenitor that has initiated trans-differentiation. The multiple HOX genes that are selectively expressed in MLL are attractive candidates for direct targets of the MLL-fusion proteins. Mll gene ablated mice have indicated that select members of the clustered Hox genes require MLL for their expression. As overexpression of HoxA9 has also been shown to induce AML in mouse models (Nakamura et al., Nat Genet 12:149–1531 (1996)), and its expression is controlled by levels of Mll (Hanson et al., Proc Natl Acad Sci USA, 96:14372–14377 (1999)); misexpression of HOXA9 may be an important component of MLL-translocation driven leukemogenesis. The findings here prompt further studies to determine if MLL-fusion proteins directly activate HOX genes, and thus lead to defects in hematopoietic differentiation.

This is the first demonstration in which whole genome profiling reveals that a chromosomal translocation can specify a unique gene expression program. This separates MLL as a distinct disease, which is of both pathogenic and therapeutic importance. Lymphoblastic leukemias with MLL translocations are recognized as having a poor prognosis, as standard ALL therapies have been relatively ineffective. The unique identity of MLL noted here provides insight into the poor response. As MLL is a distinct disease, new therapeutic approaches are needed. Of note, pilot studies have shown that addition of the drug cytarabine, an important agent in mycloid leukemia treatment, may improve the outcome for MLL patients (Ludwig et al., Blood 92:1898–1909 (1998); Silverman et al., Cancer 80:2285–2295 (1997); and Pieters et al., Leukemia 12:1344–1348 (1998)). However, it is the translocation-specific therapies which have recently proven attractive for their efficacy and lack of toxicity. Other leukemias in which a translocation specifies a distinct disease are chronic myclogenous leukemia (CML) with the BCR-ABL fusion and acute promyelocytic leukemia (APL) with the PML-RARα fusion. The tailored development of the tyrosine kinase inhibitor ST1571 and its treatment of CML and the use of all trans retinoic acid (ATRA) in APL has substantially improved the outcome in those diseases (Tallman et al., N Engl J Med 337:1021–1028 (1997) and Druker et al., N Engl J Med 344:1031–1037 (2001)). While pharmacologic approaches to the complex regulatory capacity of MLL may prove challenging, the distinct gene expression signature defined here for MLL may provide unanticipated molecular targets. Of special note, FLT3 is the most differentially expressed gene that distinguishes MLL from ALL and AML (FIGS. 5A–5D). Aberrations of FLT3, especially duplication of its juxtamembrane domain, have been noted in some cases of AML and maybe leukemogenic (Nakao et al., Leukemia 10:1911–1918 (1996); Zhao et al., Leukemia 14:374–378 (2000); and Tse et al., Leukemia 14:1766–1776 (2000)). As a tyrosine kinase receptor, FLT3 represents an attractive target for rational drug development.

Additional information regarding the methods used to carry out the above described studies, patient samples, and the differentially expressed genes identified though these studies can be found at http://research.dfci.harvard.edu/korsmeyer/MLL.htm, and http://www-genome.wi.mit.edu/MPR, the teachings of which are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of diagnosing mixed lineage leukemia, comprising determining a gene expression profile of a gene expression product from at least one informative gene from one or more cells, wherein said at least one informative gene is galectin-1, wherein the cells are selected from the group consisting of mononuclear blood cells and bone marrow cells, and wherein the gene expression profile is correlated with mixed lineage leukemia.

2. The method of claim 1, wherein the gene expression product is RNA.

3. The method of claim 2, wherein the gene expression profile is determined utilizing specific hybridization probes.

4. The method of claim 2, wherein the gene expression profile is determined utilizing oligonucleotide microarrays.

5. The method of claim 1, wherein the gene expression product is a peptide.

6. The method of claim 5, wherein the gene expression profile is determined utilizing antibodies.

7. A method of diagnosing mixed lineage leukemia, comprising:

a) determining a gene expression profile of mRNA from at least one informative gene, wherein said at least one informative gene is galectin-1, wherein the mRNA is isolated from one or more cells of an individual and selected from the group consisting of mononuclear blood cells and bone marrow cells; and b) comparing the gene expression profile of a) to a gene expression profile of a control sample, wherein the gene expression profile of a) is indicative of mixed lineage leukemia.

* * * * *